United States Patent
Vogt et al.

(10) Patent No.: US 11,981,933 B2
(45) Date of Patent: May 14, 2024

(54) ALIGNMENT OF CELLS IN ENGINEERED TISSUES

(71) Applicant: Regents of the University of Minnesota, Minneapolis, MN (US)

(72) Inventors: Caleb Darwin Vogt, Minneapolis, MN (US); Angela Panoskaltsis-Mortari, Woodbury, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 120 days.

(21) Appl. No.: 17/446,563

(22) Filed: Aug. 31, 2021

(65) Prior Publication Data

US 2022/0064603 A1 Mar. 3, 2022

Related U.S. Application Data

(60) Provisional application No. 63/072,659, filed on Aug. 31, 2020.

(51) Int. Cl.
*C12N 5/071* (2010.01)
*B33Y 10/00* (2015.01)
*B33Y 30/00* (2015.01)
*B33Y 80/00* (2015.01)
*C12N 5/00* (2006.01)

(52) U.S. Cl.
CPC ............ *C12N 5/0697* (2013.01); *B33Y 10/00* (2014.12); *B33Y 30/00* (2014.12); *B33Y 80/00* (2014.12); *C12N 5/0062* (2013.01); *C12N 2502/1347* (2013.01); *C12N 2502/23* (2013.01); *C12N 2502/28* (2013.01); *C12N 2533/54* (2013.01)

(58) Field of Classification Search
CPC ........................ C12N 5/0062; C12N 5/0697
See application file for complete search history.

(56) References Cited

U.S. PATENT DOCUMENTS

| | | | | |
|---|---|---|---|---|
| 8,852,932 B2 * | 10/2014 | Forgacs | ............... | C12N 5/0062 435/395 |
| 2004/0253365 A1 * | 12/2004 | Warren | ................. | B05C 5/0216 118/715 |
| 2022/0064603 A1 | 3/2022 | Vogt et al. | | |

OTHER PUBLICATIONS

Kelm et al. Design of custom-shaped vascularized tissues using microtissue spheroids as minimal builidng units. Tissue Engineering 2006, 12;8: 2151-2160. (Year: 2006).*
Dickman et al. Functional characterization of 3D contractile smooth muscle tissues generated using a unique microfluidic 3D bioprinting technology. FASEB Journal 2020, 34:1652-1664 (Year: 2019).*
Olsen et al. Processing cellular spheroids for histological examination. Journal of Histotechnology 2014, 37;4: 138-142. (Year: 2014).*
Annamalai et al., "Vascular Network Formation by Human Microvascular Endothelial Cells in Modular Fibrin Microtissues," ACS Biomater. Sci. Eng., vol. 2, No. 11, pp. 1914-1925, Nov. 2016.
Ashammakhi et al., "Bioinks and Bioprinting Technologies to Make Heterogeneous and Biomimetic Tissue Constructs," Materials Today Bio, vol. 1, Jan. 2019, 23 pp.
Atkins et al., "Reducing Hospital Morbidity and Mortality Following Esophagectomy," The Annals of Thoracic Surgery, vol. 78, No. 4, Oct. 2004, pp. 1170-1176.
Aubin et al., "Directed 3D Cell Alignment and Elongation in Microengineered Hydrogels," Biomaterials, vol. 31, No. 27, Sep. 2010, 22 pp.
Beamish et al., "Molecular Regulation of Contractile Smooth Muscle Cell Phenotype: Implications for Vascular Tissue Engineering," Tissue Engineering: Part B, vol. 16, No. 5, Oct. 2010, pp. 467-491.
Boudou et al., "A Microfabricated Platform to Measure and Manipulate the Mechanics of Engineered Cardiac Microtissues," Tissue Engineering: Part A, vol. 18, No. 9 and 10, Nov. 2011, pp. 910-919.
Flanagan et al., "Esophagectomy and Gastric Pull-through Procedures: Surgical Techniques, Imaging Features, and Potential Complications," Radiographics, vol. 36, No. 1, Jan.-Feb. 2016, pp. 107-121.
Garcia-Lizarribar et al., "Composite Biomaterials as Long-Lasting Scaffolds for 3D Bioprinting of Highly Aligned Muscle Tissue," Macromolecular Bioscience, vol. 18, No. 10, Oct. 2018, 13 pp.
Han et al., "Intestinal Smooth Muscle Phenotype Determines Enteric Neuronal Survival via GDNF Expression," Neuroscience, vol. 290, pp. 357-368, Apr. 2015.
Hardin et al., "Microfluidic Printheads for Multimaterial 3D Printing of Viscoelastic Inks." Advanced Materials 27:, Jun. 3, 2015, pp. 3279-3284.
Haverkamp et al., "Worldwide Trends in Surgical Techniques in the Treatment of Esophageal and Gastroesophageal Junction Cancer," Dis. Esophagus, vol. 30, No. 1, pp. 1-7, Mar. 2016.
Hayashi et al., "Vascular Network Formation for a Long-Term Spheroid Culture by Co-Culturing Endothelial Cells and Fibroblasts," in 2015 28th IEEE International Conference on Micro Electro Mechanical Systems (MEMS), Jan. 18-22, 2015, pp. 476-479.
Hinson et al., "Titin Mutations in iPS cells Define Sarcomere Insufficiency as a Cause of Dilated Cardiomyopathy," Science, vol. 349, Aug. 28, 2015, 12 pp.
Houghton et al., "Respiratory Disease and the Oesophagus: Reflux, Reflexes and Microaspiration," Nat. Rev. Gastroenterol. Hepatol., vol. 13, No. 8, pp. 445-460, Aug. 2016.

(Continued)

*Primary Examiner* — Allison M Fox
*Assistant Examiner* — Jennifer S Spence
(74) *Attorney, Agent, or Firm* — Shumaker & Sieffert, P.A.

(57) ABSTRACT

Devices, systems, and techniques are described for printing pre-aligned microtissues into larger tissue constructs. For example, a method of printing a tissue construct includes aligning cells in a first direction to create pre-aligned microtissues, suspending the pre-aligned microtissues in a liquid to create a bioink, and depositing the pre-aligned microtissues in a second direction to create the tissue construct.

13 Claims, 18 Drawing Sheets

(56) References Cited

OTHER PUBLICATIONS

Hisiao et al., "Smooth Muscle-Like Tissue Constructs with Circumferentially Oriented Cells Formed by the Cell Fiber Technology," PLoS One, vol. 10, No. 3, Mar. 3, 2015, 16 pp.
Kalman et al., "Quick and Easy Microfabrication of T-Shaped Cantilevers to Generate Arrays of Microtissues," Biomedical Microdevices, vol. 18, No. 3, Jun. 2016, 11 pp.
Kanetaka et al., "Regenerative Medicine for the Esophagus," Surg. Today, vol. 48, No. 8, pp. 739-747, Aug. 2018.
Kelm et al., "In Vitro Vascularization of Human Connective Microtissues," in Tissue Engineering, 1st ed., H. Hauser and M. Fussenegger, Eds. Humana Press, 2007 (Applicant points out, in accordance with MPEP 609.04(a), that the year of publication, 2007, is sufficiently earlier than the effective U.S. filing date, so that the particular month of publication is not in issue.) pp. 153-166.
Lee et al., "Generation of 3-D glioblastoma-vascular niche using 3-D bioprinting," in 2015 41st Annual Northeast Biomedical Engineering Conference (NEBEC), Apr. 17, 2015, pp. 1-2.
Lee et al., "Generation of Multi-scale Vascular Network System Within 3D Hydrogel Using 3D Bio-printing Technology," Cell. Mol. Bioeng., vol. 7, No. 3, pp. 460-472, Sep. 2014.
Legant et al., "Microfabricated Tissue Gauges to Measure and Manipulate Forces from 3D Microtissues," Engineering, vol. 106, No. 25, Jun. 23, 2009, pp. 10097-10102.
Luo et al., "3D Bioprinting of Artificial Tissues: Construction of Biomimetic Microstructures," Macromolecular Bioscience, vol. 18, No. 6, Jun. 2018, 9 pp.
Meng et al., "3D Bioprinted In Vitro Metastatic Models via Reconstruction of Tumor Microenvironments," Advanced Materials, vol. 31, No. 10, Mar. 2019, 19 pp.
Moldovan, "Progress in Scaffold-Free Bioprinting for Cardiovascular Medicine," Journal of Cellular and Molecular Medicine, vol. 22, No. 6, Jun. 2018, pp. 2964-2969.
Mozetic et al., "Engineering Muscle Cell Alignment Through 3D Bioprinting," Journal of Biomedical Materials Research Part A, vol. 105, No. 9, Sep. 2017, pp. 2582-2588.
Nassiri et al., "Interactions of Mesenchymal Stem Cells with Endothelial Cells," Stem Cells Dev., vol. 23, No. 4, pp. 319-332, Feb. 2014.
Nguyen et al., "Biomimetic Model to Reconstitute Angiogenic Sprouting Morphogenesis in Vitro," Engineering, vol. 110, No. 17, Apr. 23, 2013, pp. 6712-6717.
Onoe et al., "Metre-Long Cell-Laden Microfibres Exhibit Tissue Morphologies and Functions," Nature Materials, vol. 12, No. 6, Mar. 2013, pp. 584-590.
Ramade et al., Microfabrication of a Platform to Measure and Manipulate the Mechanics of Engineered Microtissues, 1st ed., vol. 121. Elsevier Inc., Feb. 2014, pp. 191-211.
Rego et al., "Bioengineered Human Pyloric Sphincters Using Autologous Smooth Muscle and Neural Progenitor Cells," Tissue Engineering: Part A, vol. 22, No. 1 and 2, Jan. 2016, pp. 151-160.
Rego et al., "Bioengineering Functional Human Sphincteric and Non-Sphincteric Gastrointestinal Smooth Muscle Constructs," Methods, vol. 99, Apr. 15, 2016, 17 pp.
Sakar et al., "Cellular Forces and Matrix Assembly Coordinate Fibrous Tissue Repair," Nature Communications, vol. 7, Mar. 16, 2016, 8 pp.
Siegel et al. "Cancer Statistics, 2019," CA: A Cancer Journal for Clinicians, vol. 69, No. 1, Jan./Feb. 2019, pp. 7-34.
Skylar-Scott et al., "Voxelated Soft Matter via Multimaterial Multinozzle 3D Printing," Nature 575, Nov. 13, 2019, pp. 330-335.
Tomalka et al., "Porcine Stomach Smooth Muscle Force Depends on History-Effects," Frontiers in Physiology, vol. 8. No. 802, Oct. 2017, 12 pp.
Trebbin et al., "Anisotropic Particles Align Perpendicular to the Flow Direction in Narrow Microchannels," Engineering, vol. 110, No. 17, Apr. 23, 2013, pp. 6706-6711.
Wang et al., "Gap Junctions in Gastrointestinal Muscle Contain Multiple Connexins," American Journal of Physiology—Gastrointestinal and Liver Physiology, vol. 281, No. 2, Aug. 1, 2001, pp. G533-G543.
Wang et al., "Necking and Failure of Constrained 3D Microtissues Induced by Cellular Tension," Engineering, Dec. 9, 2013, 6 pp.
Wenger et al., "Development and Characterization of a Spheroidal Co culture Model of Endothelial Cells and Fibroblasts for Improving Angiogenesis in Tissue Engineering," Cells Tissues Organs, vol. 181, No. 2, pp. 80-88, Nov. 2005.
West et al., "Development and Characterization of a 3D Multicell Microtissue Culture Model of Airway Smooth Muscle," American Journal of Physiology. Lung Cellular and Molecular Physiology, vol. 304, No. 1, Jan. 2013, 29 pp.
Wilgenbus et al., "Expression of Cx26, Cx32 and Cx43 Gap Junction Proteins in Human Normal and Neoplastic Tissues," Int. J. cancer, vol. 52, pp. 1-8, Jan. 1992.
Yu et al., "Three-Dimensional Bioprinting Using Self-Assembling Scalable Scaffold-Free "Tissue Strands" as a New Bioink," Scientific Reports, vol. 6, No. 1, Jun. 2016, 11 pp.
Zifan et al., "Three-Dimensional Myoarchitecture of the Lower Esophageal Sphincter and Esophageal Hiatus Using Optical Sectioning Microscopy," Scientific Reports, vol. 7, Oct. 13, 2017, 8 pp.

* cited by examiner

ALIGNMENT OF CELLS IN ENGINEERED TISSUES

This application claims the benefit of U.S. Provisional Patent Application No. 63/072,659, filed 31 Aug. 2020, the entire contents of which is incorporated herein by reference.

GOVERNMENT INTEREST

This invention was made with government support under T32HL007741, R21EB022830, and T32GM008244 awarded by National Institutes of Health. The government has certain rights in the invention.

TECHNICAL FIELD

This disclosure relates generally to methods, systems, and devices for engineering tissue.

BACKGROUND

Biological tissues are highly ordered by means of cell layers, cellular alignment, or both. The precise structural arrangement of cells is critical to all tissue function. Mechanically active tissues including skeletal muscle, smooth muscle, cardiac muscle, tendons, and ligaments are all soft tissues structured with elongated cells that are aligned in the direction of the greatest stress. In long skeletal muscles and tendons, all cells are aligned in a single direction. However, cardiac muscle and the smooth muscle of the gastrointestinal and urogenital systems have layers of muscle with multiple directions of alignment.

SUMMARY

This disclosure describes example techniques and systems for making and using three dimensional (3D)-printed model biological microenvironments. Examples of the present disclosure include generating long and pre-aligned microtissues, suspending the microtissues in a bioink, and printing the bioink with microtissues using a 3D extrusion bioprinter. These pre-aligned microtissues may thus be assembled into larger, macroscale tissues using technologies including 3D-bioprinting. A scaffolding material (e.g., a biocompatible polymer or biopolymer) may be used to create a desired shape, and the microtissues with pre-aligned cells can be added to create an immature "tissue construct." The tissue construct may then be matured in a bioreactor that applies chemical, electrical, and mechanical stimulation to cause maturation of the tissue into the desired final form, such as connective tissue that includes smooth or skeletal muscle, tendons, ligaments, or any other tissues.

The microtissues may be pre-aligned in that the microtissues are formed using cells that align in one direction. These pre-aligned microtissues may then be suspended in a liquid (e.g., hydrogel) material to create a "bioink," that may be used in a 3D bioprinter. Laminar flow physics and geometric constraints cause the microtissues to align with each other in the same or different direction as they are extruded out of the nozzle of the printer; resulting in direct writing of aligned cellular bundles. This enables for creation of complex layers and patterns having any desired alignment of cells. This process also enables for creation of all types of cellular alignment found in muscle, tendon, and ligament tissues in the body, including the highly complex structures found in the cardiovascular, gastrointestinal, and urogenital systems.

In some examples, a method of printing a tissue construct includes aligning cells in a first direction to create pre-aligned microtissues; suspending the pre-aligned microtissues in a liquid to create a bioink; and depositing the pre-aligned microtissues in a second direction to create the tissue construct.

In another example, a 3D-printed tissue construct includes a plurality of pre-aligned microtissues, each pre-aligned microtissues comprising cells aligned in a first direction, wherein the plurality of pre-aligned microtissues deposited via a bioink in a second direction to form the 3D-printed tissue construct.

In another example, a system for printing a tissue construct, the system including a first bioreactor configured to mature and align cells in a first direction to create pre-aligned microtissues; a printer nozzle configured to deposit the pre-aligned microtissues in a second direction to create the tissue construct; and a second bioreactor to mature the tissue construct.

The details of one or more embodiments of the disclosure are set forth in the accompanying drawings and the description below. Other features, objects, and advantages of the disclosure will be apparent from the description and drawings, and from the claims.

DETAILED DESCRIPTION

Figure 1:
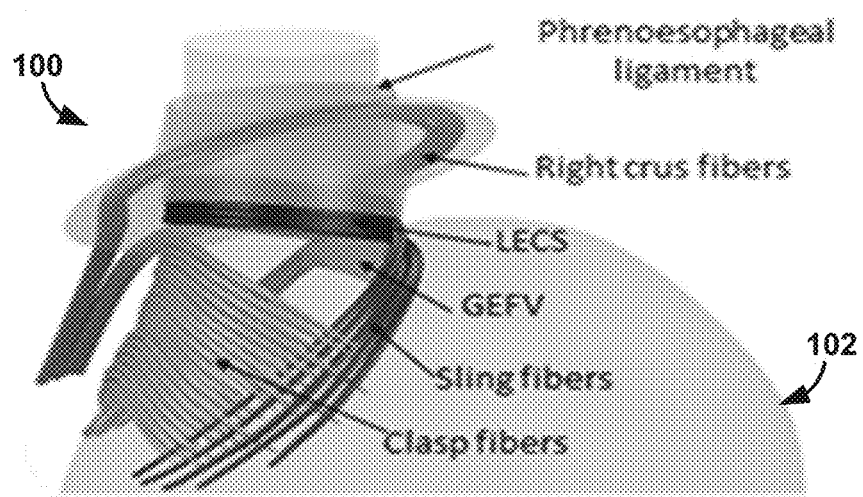
FIG. 1 is a graphical representation of an example gastroesophageal junction (GEJ) GEJ fascicle arrangement with a thick inner circular muscle layer of the esophagus continuous with bundles of smooth muscle in accordance with the examples of this disclosure.

In general, this disclosure describes examples of 3D-printed biological environments, and example techniques for making and using such example 3D-printed biological microenvironments. Biological tissues are highly ordered by means of cell layers, cellular alignment, or both. As one example, natural muscle tissue generally exhibits a high degree of alignment that allows for efficient directional force generation. The precise structural arrangment of cells important to all tissue function. Mechanically active tissues including skeletal muscle, smooth muscle, cardiac muscle, tendons, and ligaments are all soft tissues structured with elongated cells that are aligned in the direction of the greatest stress. In long skeletal muscles and tendons, all cells are aligned in a single direction. In cardiac muscle, the smooth muscle of the gastrointestinal system, and urogenital systems have layers of muscle with multiple directions of alignment. Recreating the more complex structures found in these cardiac and smooth muscle tissues may be very difficult. Examples of the present disclosure discuss incorporating pre-aligned microtissues into a 3D bioprinting "bioink" to recreate complex muscle sturctures.

Cell alignment is a challenge in tissue engineering. Examples of the present disclosure disclose pre-alignment of cells within microtissues that may then be assembled into larger, macroscale tissues using technologies including 3D-bioprinting. Microtissues that contain cells that are all aligned within the microtissue structure may be subassemblies that are then assembled into larger tissues. These microtissues may be used to form the desired alignment structures including complicated tissue structures such as the GEJ.

Cellular alignment, in one direction, may be performed using geometric cues, remote fields, passive mechanics, and active mechanics. This process may be performed by creating a desired shape out of a scaffolding material (e.g., typically made from a biocompatible polymer or biopolymer), and to that cells are then added. This creates an immature "tissue construct". This construct may then be matured in a bioreactor that applies signals including chemical, electrical, and mechanical stimulation to cause maturation of the tissue into a desired final form. One of the limitations of this method is it is only able to produce one direction of cell alignment within tissues. The resulting tissue constructs are of limited complexity and are limited in physical scale.

In examples of the present disclosure, bioreactor signals, including chemical, electrical, and mechanical stimulation, may be applied at the beginning of the process rather than the end. Mature microtissue "building blocks" using cells are created up front. A scaffold may then be deposited with microtissues in the desired shape. The microtissues are then matured in a bioreactor. This unidirectional cell alignment may be applied on the micron scale to create small pieces of pre-aligned tissue. These small tissues are then assembled into larger aligned tissues through the use of three-dimensional (3D) bioprinting technology. In one example, active mechanics may be used to create small, cylindrically shaped tissues with approximate dimensions of 300 microns in length and 100 microns in width. These microtissues, that are longer than they are wide, may be made of cells aligned with the primary axis of the microtissue.

These microtissues may then be suspended in a hydrogel material to create a bioink that may be used in a 3D bioprinter. Laminar flow physics and geometric constraints can cause the microtissues to align in the direction of flow and/or with each other as they are extruded out of the nozzle of the printer, resulting in direct writing of aligned cellular bundles. Examples of the present disclosure enable for creation of complex muscle layers and patterns of alignment. This enables for recreation of all types of cellular alignment found in muscle, tendon, and ligament tissues in the body, including the highly complex structures found in the cardiovascular, gastrointestinal, and urogenital systems.

Cancer of the gastrointestinal system, such as gastroesophageal adenocarcinoma, is a significant source of morbidity and mortality, with an estimated 200,000 new cases in the United States in 2019. For cancers involving the alimentary canal (e.g., esophagus, stomach, intestines), surgical resection of the cancer and anastomosis of the cancer-free portions of the tube is the best treatment if the tumor is small. The GEJ may be treated in this manner with a surgery known as gastric pull-up; however, patients may experience complications after the procedure. Loss of the GEJ's anatomical barrier to reflux may lead to pulmonary complications. Thus, while simple resection and anastomosis is attractive in some regions of the alimentary canal, there is an urgent need for new solutions at the GEJ. Recent developments in induced pluripotent stem cells raise the possibility that patient-specific autografts may be tissue-engineered. Clinical trials have successfully replaced portions of the esophagus with tissue-engineered products. Despite these apparent successes, almost no work has been done to rebuild the GEJ. Of the hurdles preventing the field from progressing, anatomical complexity of the muscles structure and the need for vascularization are the most pressing. As described herein, pre-aligned microtissues used for 3D printing of larger tissue constructs may enable the creation of various anatomical structures, such as the GEJ. 3D printing of pre-aligned microtissues may enable the creation of any other types of tissues in other examples.

Generally, the microtissues described herein may be comprised of mammalian cells (human or non-human). However, in other examples, the techniques described herein may also be performed using non-mammalian cells, such as plant cells. In some examples, plant cells may be used to generate various constructs suitable for pharmaceuticals and/or delivery of pharmaceuticals.

FIG. 1 is a graphical representation of an example gastroesophageal junction (GEJ) 100 fascicle arrangement in accordance with the examples of this disclosure. The GEJ 100 differs from the rest of the alimentary canal in its complex arrangement of smooth muscle bundles. At the GEJ 100, there is a thickening of the inner circular muscle layer of the esophagus that is continuous with bundles of smooth muscle in the stomach wall known as gastric sling fibers. These fibers are opposed by gastric clasp fibers on the lesser curvature of stomach 102. All three of these components have specific mechanical roles and contract in unison to maintain the anti-reflux barrier at the GEJ 100. A feature to achieving contractile function is highly aligned gut smooth muscle cells (gSMCs) within these bundles. As described further below, printing pre-aligned microtissues into larger tissue constructs may enable creating of the GEJ 100 with highly aligned gSMCs that provide the functionality of the GEJ 100.

Figure 2:
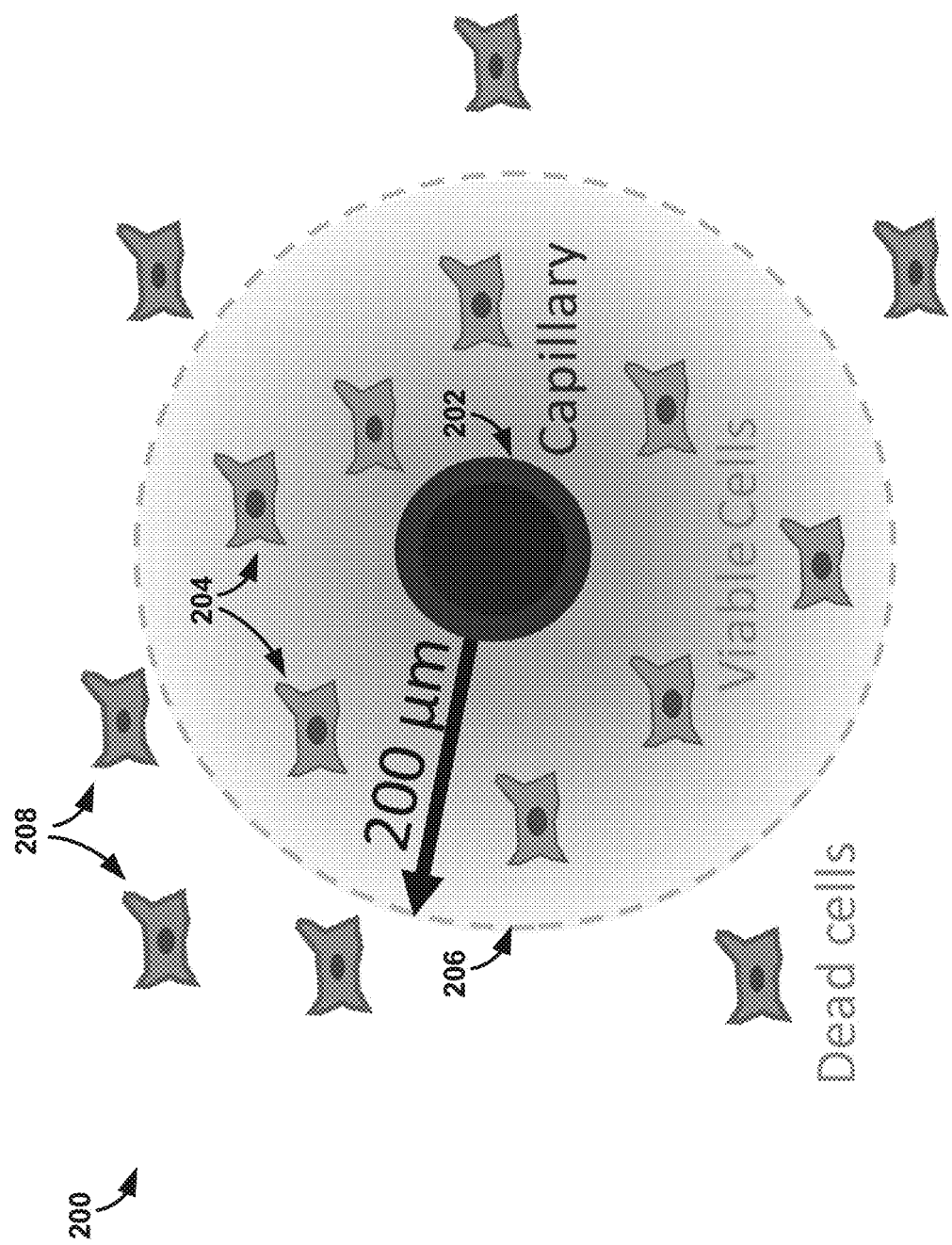
FIG. 2 is a graphical representation of an example vascularization in accordance with the examples of this disclosure.

FIG. 2 is a graphical representation of an example vascularization in accordance with the examples of this disclosure. Vascularization (e.g., the process of forming blood vessels) is a challenge in tissue creation in system 200. For example, the wall thickness at the GEJ ranges from approximately 2 millimeters (mm) to 6 mm, but the diffusion limit of oxygen is only 200 micrometers (µm), as shown as boundary 206, from the oxygen source 202. Without capillary beds throughout the construct, widespread necrosis may ensue. In other words, cells 208 beyond boundary 206 die while only cells 204 within boundary 206 survive. As such, there is a "race" between angiogenesis/vasculogenesis (i.e., the development of new blood vessels) and necrosis in engineered tissues. The tissue engineering field has developed methods for pre-vascularization of tissue, but these methods typically rely on generating capillary beds within small or thin pieces of tissue, that may have to be assembled together to make thicker tissues. Three dimensional (3D) bioprinting has led to new methods for creating large channels (e.g., 300 µm diameter) that may approximate arterioles and venules, but do not produce vessels small enough to resemble capillaries. Because small capillaries are important for obtaining the vascular surface area necessary to keep tissue alive, these large channels are not enough to solve the vascularization problem. Therefore, while the field has made progress in vascularization, creating thick tissues required for the GEJ remains a challenge.

Over 200,000 people in the United States are predicted to develop cancer of the alimentary tract (e.g., the esophagus, stomach, intestines) in the United States in 2019. Surgical resection is often the preferred method of treatment, but it may lead to loss of normal function within the tract. A key anatomical region is the GEJ, that performs one-way valve function to keep stomach contents from refluxing into the esophagus. Surgical removal of the GEJ and anastomosis of the stomach to the esophagus in a gastric pull-up procedure is associated with significant morbidity and mortality, with up to 20% of patients experiencing respiratory complications post-surgery due to stomach contents rising high into the upper esophagus and into the trachea as micro-aspiration. Tissue-engineered solutions may be ideal for replacing the GEJ, but as discussed there are numerous challenges. Recreating the complex arrangement of gSMC bundles at the GEJ may not be done with current methods, and vascularization of tissue-engineered constructs remains a challenge. The individual gSMCs at the GEJ exhibit a high level of alignment within the bundles, allowing each bundle to maximize its force production. These bundles are wrapped in numerous configurations around the GEJ and work together to maintain a high-pressure zone that resists reflux. Because this tissue is metabolically active, it requires substantial blood flow. 3D bioprinting can make medium vascular channels (e.g., 200 µm diameter) but efficiently making capillaries (e.g., 8 µm diameter) to increase the surface area required for mass transfer remains difficult. As described herein, printing microtissues with pre-aligned cells supplemented with vascular cells may enable the creation of such smaller blood vessels and capillaries that may be able to provide blood flow to the larger printed tissue construct.

Figure 3:
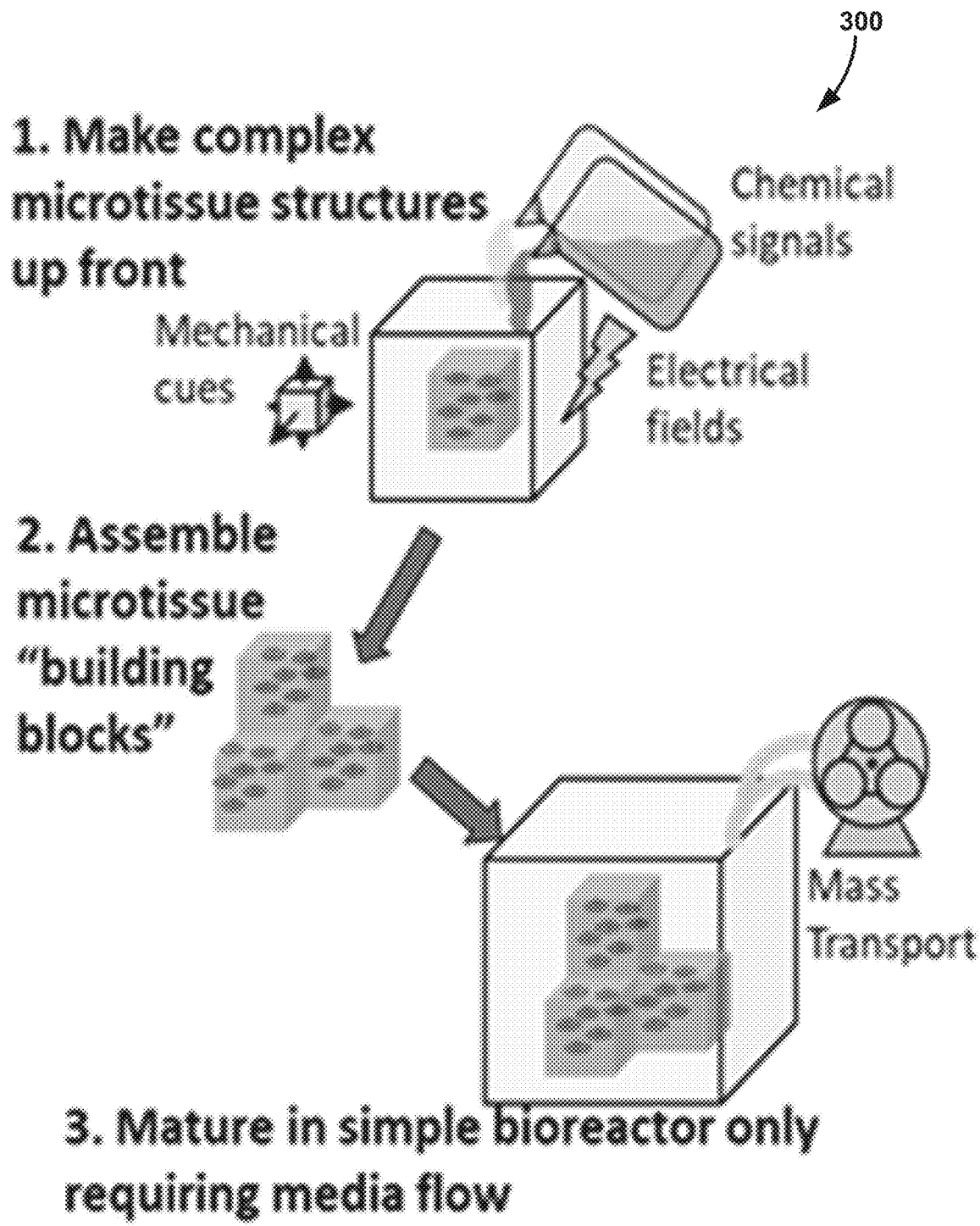
FIG. 3 is a graphical representation of an example tissue engineering process for aligned and vascularized smooth muscle tissue where a scaffold and combination of cells is then placed into a custom bioreactor to provide a final matured structure in accordance with the examples of this disclosure.

FIG. 3 is a graphical representation of an example tissue engineering process 300 for aligned and vascularized smooth muscle tissue where a scaffold and combination of cells is then placed into a custom bioreactor to provide a final matured structure in accordance with the examples of this disclosure. Examples of this description include an approach that re-arranges the traditional tissue engineering process. Some methods to align muscle cells or create capillary vasculature can work on small tissue sizes but may not be scaled-up to produce large constructs. This is because the traditional approach is to add cells into a scaffold that provides shape, then mature the construct in a complex bioreactor. This may not work for the GEJ or other structures, because of the complex alignment of gSMC bundles. Furthermore, creating capillaries traditionally relies on placing endothelial cells in the constructs and hoping they may form a network before necrosis sets in at the center of thick tissues. Rather than scaling-up the size of existing methods, examples of the present disclosure produce pre-aligned and pre-vascularized microtissues, that may then be used in a 3D bioprinter as "building blocks" to make larger tissue constructs. This approach may move much of the tissue maturation process to the beginning of the process, such as in the creation of the initial microstructures with pre-aligned cells that can be used in bioink, rather than the end. This pre-alignment of cells may greatly decrease the complexity during final maturation in a bioreactor. Bioprinting of pre-matured microtissues (and in some cases including pre-aligned c ells) may result in enhanced control over tissue alignment and vascularization.

Bioprinting pre-aligned microtissues may result in greater alignment and active force generation in the aligned direction when compared to traditional bioprinting. The microtissues may be formed by strain-induced (e.g., mechanical cues to the cells) alignment of gSMC-laden collagen hydrogels. The phenotype of the gSMCs in the microtissues and overall tissue maturity may be assessed by expression of key proteins.

Printing a tissue with pre-vascularized microtissue bioink may result in faster development of capillary networks compared to traditional freely suspended cell bioprinting. Microtissues with gSMCs and fluorescent human umbilical vein endothelial cells (hUVECs) may be made by spheroid culture. The effects of gSMCs and culture conditions on sprouting of hUVECs from the spheroid into a collagen gel may be measured. These microtissues may be printed between two perfusable large vascular channels and cultured to form a capillary network that connects the two larger channels. Dextran diffusion through the network may be used to compare flow to control, that may be a traditional 3D bioprinting of gSMCs and endothelial cells suspended as individual cells within the bioink.

Examples of the present disclosure disclose reimagining the conventional workflow of tissue engineering. These aims may be combined to provide the field with a new, unified approach to generating smooth muscle. These examples may be broadly applicable to tissue engineering in the alimentary tract and may apply to other challenges such as establishing neural control. Examples of the present disclosure may be extended to applications in other aligned, vascularized tissues, such as cardiac muscle.

Traditional tissue engineering relies on first producing a scaffold that defines a shape that may be populated by cells. This combination of cells and scaffold is then placed into a custom bioreactor to try to provide the necessary cues to form the final matured structure. Traditional extrusion bioprinters use a "bio-ink" made from a hydrogel precursor loaded with individually suspended cells that is extruded out of a nozzle to create the cell-laden structure.

Figure 4:
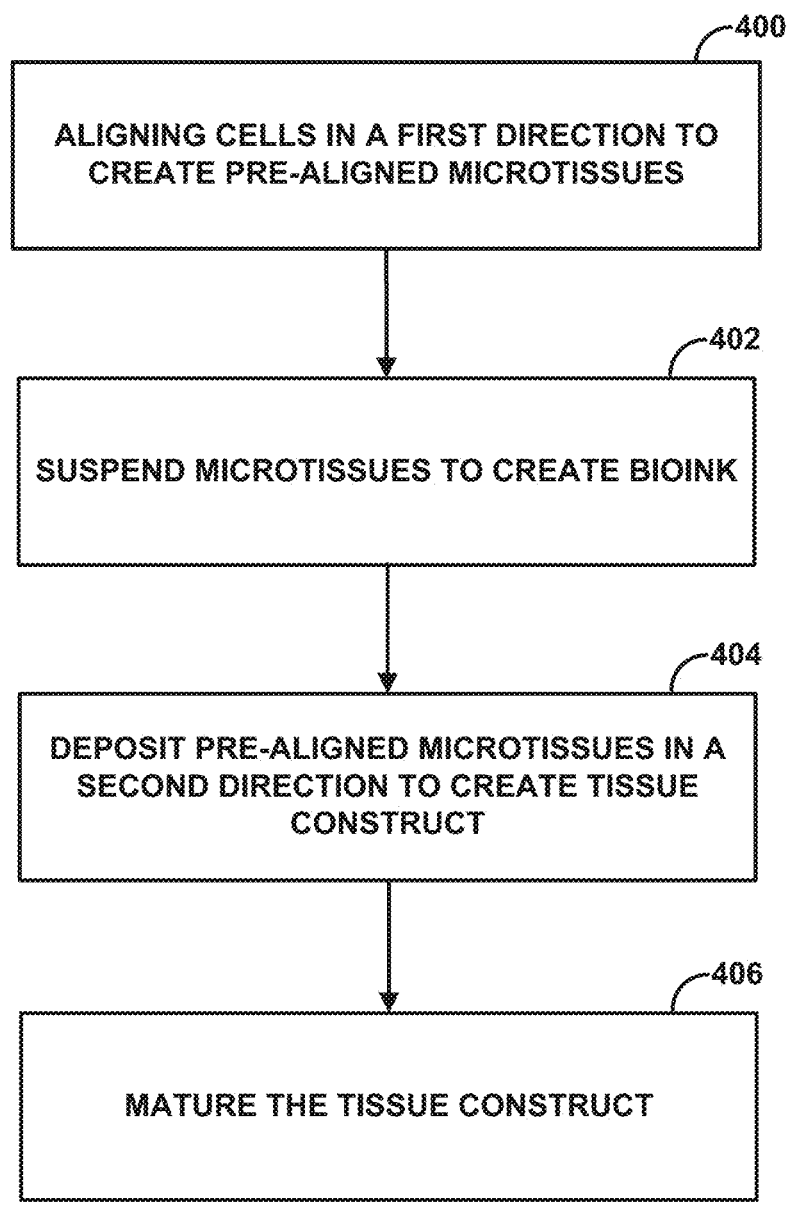
FIG. 4 is a flow diagram of an example technique for creating pre-aligned microtissues and larger tissue constructs.

FIG. 4 is a flow diagram of an example process for a method of 3D-printing a 3D-printed microenvironment in accordance with the present description. In the example of FIG. 4, an operator aligns cells in a first direction to create pre-aligned microtissues (400). In one example, muscle cells may be matured using bioreactor signals so that the muscle cells are aligned in the first direction to form one or more aligned microtissues. For instance, aligned muscle cells may be formed by suspending cell-laden hydrogels between attachment structures in small wells of a substrate. In one example, each of the wells have rubber posts at each end of each well. As cells remodel the hydrogel, they may cause the gel to undergo compaction, inducing a strain in the hydrogel between the two anchoring posts. The muscle cells align with their long axis parallel to the strain, resulting in highly aligned microtissues. In other examples, different structures other than posts may be used. For example, attachment structures may include microgrooves, other tissue suspended between edges or ends of structures, and/or any other structure that may constrain cells in a single direction. When released from the attachment points (e.g., cut from the posts or cut from other tissue at ends of a channel), the resulting microtissues include pre-aligned cells and may be ready to be printed, or deposited, into desired shapes. In some examples, microtissues may be created to have widths or diameters from approximately 100 μm to approximately 200 μm, but smaller or larger widths may be used in other examples. In some examples, microtissues may be created to have lengths from approximately 5 mm to approximately 10 mm, but smaller or larger lengths may be used in other examples. In other examples, microtissues may be formed with pre-aligned cells using techniques other than strain between posts, such as using grooved (nanogroove) patterning of wells, electrical field alignment, or chemical alignment.

The pre-aligned microtissues can then be combined (e.g., suspended) with a liquid (e.g., liquid or gel) to create a bioink (402). For instance, for aligned tissue bioprinting, pre-aligned microtissues (e.g., microtissues with a diameter of 250 μm and a length of 1 cm) may be aligned in the printing direction when printed as a suspension in GelMA bioink (See FIG. 9B).

A nozzle may then deposit the bioink laden with pre-aligned microtissues into a larger tissue construct of a desired orientation (e.g., a desired direction of alignment that may be different than the direction of alignment of cells within each microtissue) (404). For instance, rather than scaling-up the size of existing methods, pre-aligned and pre-vascularized microtissues may be produced and then used as "building blocks" in a 3D bioprinter to make larger tissue constructs. This approach may move much of the tissue maturation process to the beginning of the process (e.g., creating the microtissues used in the bioink) rather than the end (after all cells are printed in the desired shape of the tissue construct). This may greatly decrease the complexity during final maturation in a bioreactor. Bioprinting of pre-matured microtissues may result in enhanced control over tissue alignment and vascularization. In some examples, the nozzle may enable printing a 3D structure with the pre-aligned microtissues being deposited across two-dimensions and in height to create the 3D tissue construct. In other examples, the nozzle may be used to print multiple two-dimensional layers of microtissues, and then the different two-dimensional layers can be arranged and layered as desired to create a 3D larger tissue construct.

The larger tissue construct may then be matured in a bioreactor (406). Although, the approach discussed above may move much of the tissue maturation process to the beginning of the process rather than the end, final maturation of the tissue construct may be needed to grow the tissue construct and enable functionality and stability between the deposited microtissues. Bioprinting of pre-matured and pre-aligned microtissues may result in enhanced control over tissue alignment and vascularization. This may greatly decrease the complexity during final maturation of the tissue construct in a bioreactor.

Figure 5:
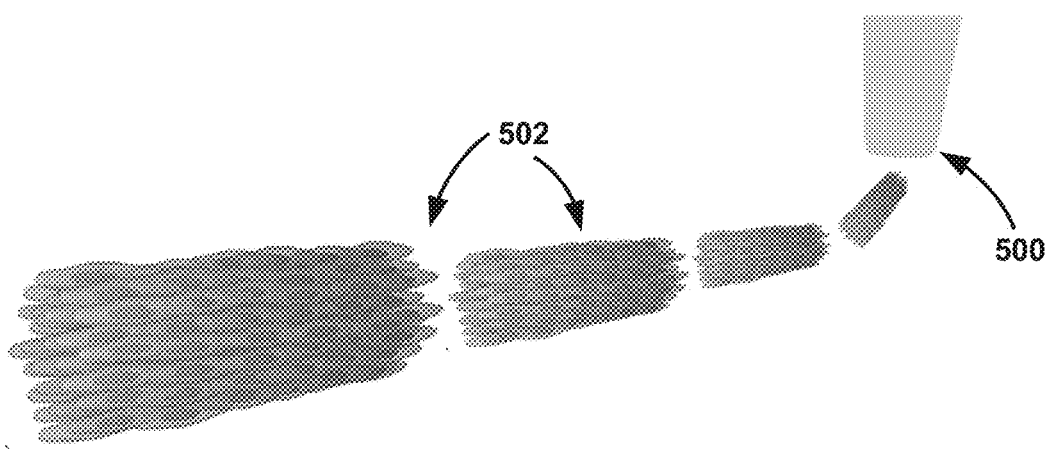
FIG. 5 is a graphical representation of pre-aligned microtissues in accordance with the example of this disclosure.

FIG. 5 is a graphical representation of pre-aligned microtissues 502 in accordance with the example of this disclosure. The problem for creating the GEJ using such a workflow is that making a bioreactor to achieve the complex anatomical structure and also induce vascularization is prohibitively complex. Examples of the present disclosure may rearrange existing techniques to create mature microtissues, accomplishing the most complex parts of the process while the tissues are still on a manageably small scale. These pre-matured and pre-aligned microtissues 502 may then be used as the building blocks to create larger tissues that do not require a complicated bioreactor to achieve alignment and vascularization (See FIG. 2). For the purpose of printing aligned gSMC bundles, an advanced bio-ink may be made from pre-aligned microtissues 502, rather than individually suspended cells as is done in traditional bioprinting. A combination of geometric constraints and fluid flow alignment may be used to print the microtissues 502 end-to-end as they are released from printing nozzle 500. In some examples, microtissues 502 can then fuse to form a fascicle or bundle of structures. Examples of the present disclosure disclose a tissue engineering method allowing for continuous extrusion bioprinting of smooth muscle bundles that are similar to those found in the native GEJ.

Figure 6:
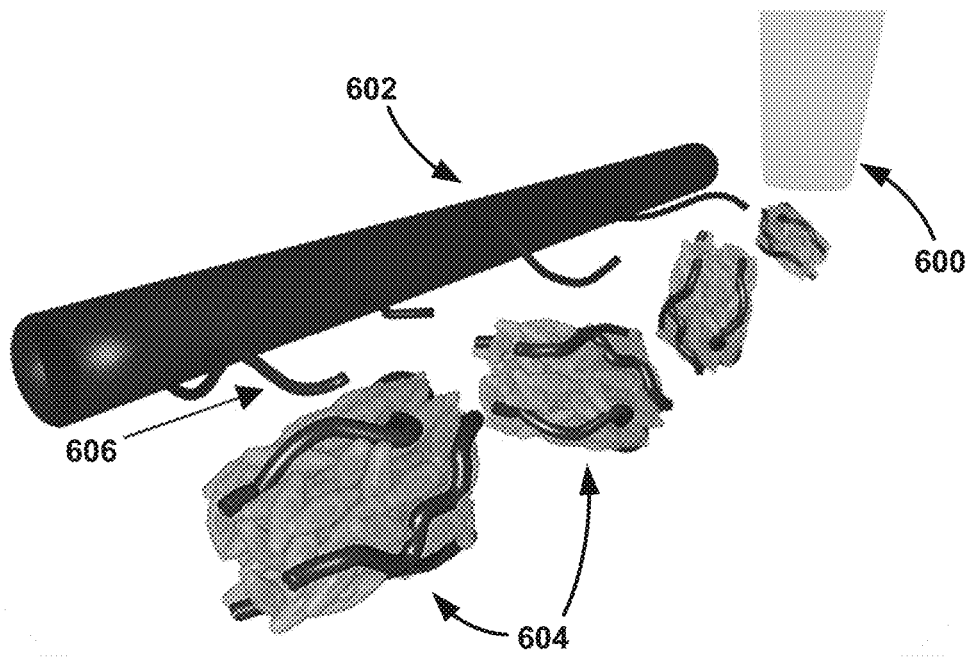
FIG. 6 is a graphical representation of pre-vascularized microtissues in accordance with the example of this disclosure.

FIG. 6 is a graphical representation of pre-vascularized microtissues 604 in accordance with the example of this disclosure. To address the vascularization problem, pre-vascularized gSMC microtissues 604 may be created by co-culturing gSMCs with endothelial cells in pre-aligned microtissues. Such pre-vascularized and pre-aligned microtissues 604 have not been applied before in bioprinting. These pre-vascularized microtissues may be suspended in a bio-ink and used to print, from printing nozzle 600, a macroscopic tissue that also contains large (e.g., 200 μm diameter, 300 μm diameter, or greater) vascular channels 602. Angiogenic sprouting 606 may occur between vascular channels 602 and pre-vascularized microtissues 604. For example, maturation may lead to connections forming between the short capillary structures found within the microtissues 604, and between the microtissues 604 and the large printed channels 602. The result may be a tissue engineering method for creating vascularized tissue that is connected to larger bioprinted channels.

Bioprinting pre-aligned microtissues may result in greater alignment and active force generation in the aligned direction when compared to traditional bioprinting. Cell alignment is important for muscular contraction on the tissue level, because muscle tissue is largely incompressible and therefore may not change shape if contracted in all directions at once. A simple method to achieve cell alignment in tissue is through mechanical strain induction. Smooth muscle cells may be highly sensitive to strain and tend to align either parallel or perpendicular to applied strain, depending on various factors. 3D tissues with aligned cells may be formed by suspending cell-laden hydrogels in small wells between rubber posts. As cells remodel the hydrogel, they cause the gel to undergo compaction, inducing a strain in the gel between the two anchoring posts. The cells align with their long axis parallel to the strain, resulting in highly aligned tissues. When released from the anchoring posts, this may yield cylindrically shaped microtissues of aligned cells that may be suspended in a bio-ink for printing.

The microtissues being extruded in alignment may be the result of two physical phenomena. First, the microtissues may be geometrically constrained by the printer nozzle. If the nozzle is only slightly larger than the diameter of the microtissue cylinder, the tissues must pass through in an end-first orientation. Second, there is a well-established alignment phenomenon that is observed when cylindrical particles travel in laminar flow. If the flow is passing through a smoothly narrowing passage, the particles align with their long axis parallel along the flow streamlines. Because bioprinting nozzles may have a tapering feature, this flow-aligning effect is expected to contribute to microtissue alignment as they approach the end of the nozzle, preparing them for end-first passage. While these physics principles are established, they have not been used for creating aligned tissues in this manner.

The smooth muscle cells that make up the muscular tissue in the alimentary canal are not homogeneous in their phenotype, making cell selection important. These phenotypic differences lead to differences in resting tone and stimulated contractile force generation. In an example of the present disclosure, human esophageal smooth muscle cells (heSMCs) may be used. HeSMCs do not have significant resting tone compared to the tonically contracted cells of the GEJ. Therefore, heSMCs may have a greater dynamic range in their contraction force, increasing the signal-to-noise ratio in any experiments involving contractile force generation in response to a stimulus.

Figure 7A:
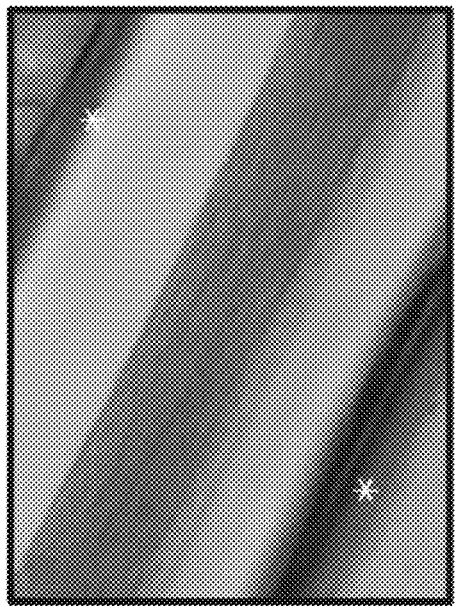
FIGS. 7A and 7B are a pictorial representation illustrating example meso-scale tissues maturing from individual cells in a collagen gel within a single long, linear well at day 0 and 5, respectively, demonstrating cell compaction and alignment where asterisks denote the side walls of the wells in accordance with the examples of this disclosure.
Figure 7B:
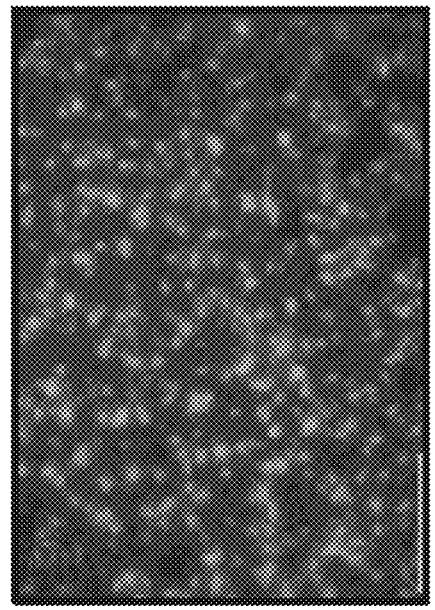
Figure 7C:
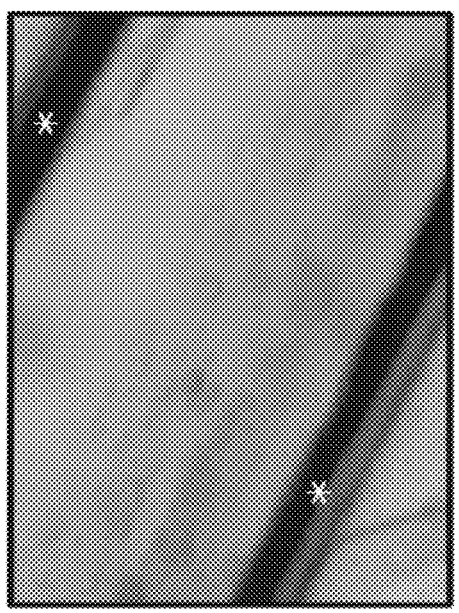
FIG. 7C is a pictorial representation illustrating Hoechst staining of example aligned tissue in accordance with the examples of this disclosure.
Figure 7D:
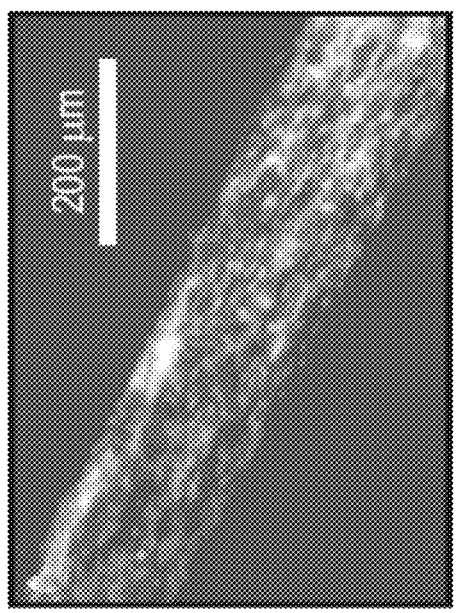
FIG. 7D is a pictorial representation of an example control unaligned tissue demonstrate in accordance with examples of this disclosure.
Figure 7E:
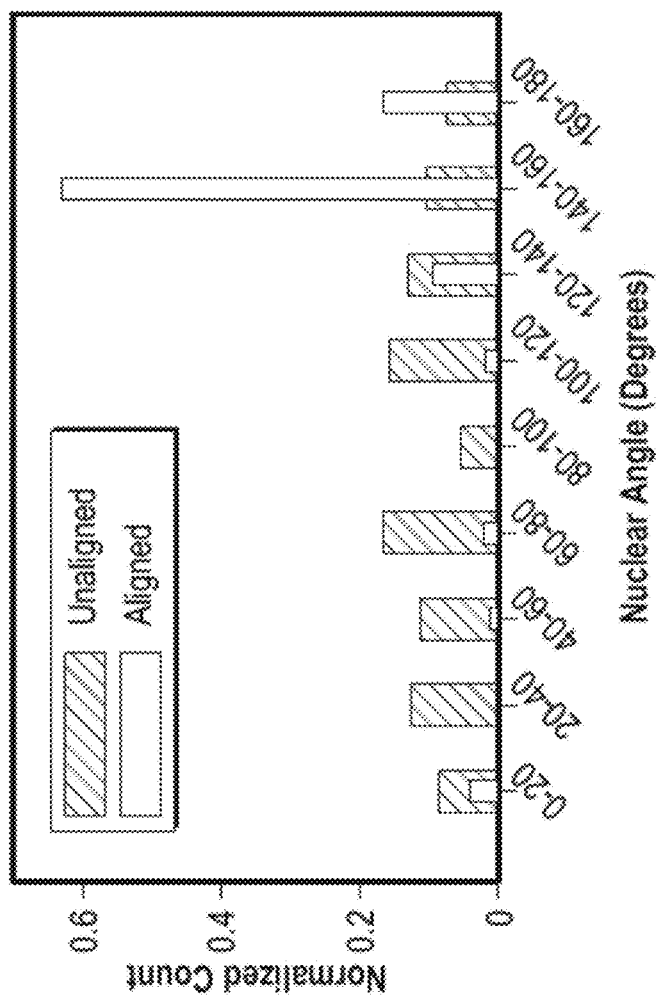
FIG. 7E is a table representation of example clustering of nuclear angles in an aligned case in accordance with examples of this disclosure.
Figure 7F:
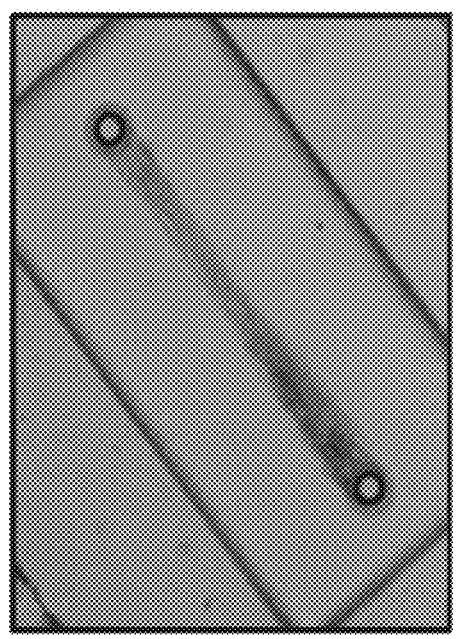
FIG. 7F is a pictorial representation of an example fabricated PDMS microwell with an aligned SMC microtissue suspended between two posts in accordance with examples of this disclosure.

FIG. 7F is a pictorial representation of a fabricated PDMS microwell with an aligned SMC microtissue suspended between two posts in accordance with examples of this disclosure. The effect of 3D aligned microtissue on smooth muscle cell (SMC) phenotype aligned microtissues may be produced in a custom microdevice consisting of an array of small rectangular wells with posts at either end. The device may be manufactured by using a negative mold that polydimethyl-siloxane (PDMS) may be cast to form the positive well and post features. The well and post features (See FIG. 7F) may be produced in an array across the surface of the microdevice that may fit within a 100 $cm^2$ petri dish. The rectangular wells may have dimensions of, for example 800×400 μm and a depth of 100 μm. The microwell array may be filled with heSMCs suspended, for example, in a 2% collagen hydrogel at a density of 5×10$^5$ cells/mL. This solution may be pipetted onto the surface of the microwell array and centrifuged at 200 g to cause the cell-laden gel to fill the microwells. Excess solution may be aspirated from the edge of the array. The developing microtissues may be cultured in a 37° C. incubator for 7 days. The heSMCs contract the collagen gel, pulling on the posts microwells and causing strain-induced alignment.

FIG. 7E is a table representation of a clustering of nuclear angles in an aligned case in accordance with examples of this disclosure. HeSMC viability and proliferation within the tissue may be quantified by fluorescent LIVE/DEAD staining (Live Dead assay staining solution is a mixture of two fluorescent dyes that differentially label live and dead cells) and staining for Ki-67 (antigen KI-67 is a nuclear protein that is associated with cellular proliferation) and BrdU incorporation (indicators of cell division). Cell alignment within the microtissues may be quantified using immunofluorescent microscopy by measuring nuclear angles. Cell nuclei may be stained with DAPI (4',6-diamidino-2-phenylindole, is a fluorescent stain that binds strongly to adenine—thymine-rich regions in DNA). FIG. 7E represents an example of the measure the angle between the long axis of each nucleus and the axis between the anchoring posts. Only the nuclei found suspended between the posts in randomly selected wells may be used for these quantifications. These measures may be compared against an unaligned control made of heSMCs cast at the same density and cultured in the same manner as the microtissues but cast into a 96-well plate, that may not result in a preferred direction of alignment.

Smooth muscle cells may come in two terminal phenotypes: synthetic or contractile. Synthetic phenotype cells are involved in the growth of smooth muscle tissue, and contractile phenotype cells are responsible for force generation. Microtissues may be examined by immunofluorescence (IF) microscopy for expression of alpha smooth muscle actin (αSMA) and smooth muscle myosin heavy chain (SM-MHC). αSMA is expressed by both phenotypes, but SM-MHC is specific for the contractile phenotype. Semi-quantitative and quantitative measurements of SM-MHC and αSMA expression may be made by Western blot analysis (is a widely used analytical technique in molecular biology and immunogenetics to detect specific proteins in a sample of tissue homogenate or extract) and Real-Time Quantitative Reverse Transcription PCR (qRT-PCR enables reliable detection and measurement of products generated during each cycle of polymerase chain reaction process), respectively. These methods may be used to compare expression of Connexin 43 (a gap junction protein) that may help to assess muscle cell interconnectivity and overall tissue maturity. Controls include 2D cultures of synthetic heSMCs [e.g., 10% serum medium and basic fibroblast growth factor (bFGF)] and contractile heSMCs [e.g., serum-free medium with transforming growth factor $\beta_1$ (TGF-$\beta_1$)], and a 3D unaligned gel with heSMCs. Comparing the microtissue expression of SM-MHC to the synthetic and contractile control groups may provide insight as to where the microtissue as a whole is sitting in the continuum between purely synthetic and purely contractile phenotypes, and the effect of 3D aligned and unaligned culture environments.

FIG. 7A and 7B are a pictorial representation illustrating meso-scale tissues maturing from individual cells in a collagen gel within a single long, linear well at day 0 and 5, respectively, demonstrating cell compaction and alignment where asterisks denote the side walls of the wells in accordance with the examples of this disclosure. Examples of the present disclosure demonstrate that heSMCs may undergo strain-induced alignment by remodeling collagen gels in both microscale (e.g., diameter 100 μm, length 600 μm) and slightly larger mesoscale (e.g., diameter 250 μm, length 1 cm) tissues (See, FIGS. 7A, 7B, 7C, and 7D). The microscale tissues were formed in microwells as described above. The mesoscale tissues were produced in larger molds that may be made by 3D printing, rather than photolithography as required by the microscale molds. Alignment may be demonstrated by analysis of nuclear angles and comparison to heSMCs in an unaligned collagen gel. The microscale tissues (See FIG. 7F) may be freed from the wells using laser micro-dissection.

FIG. 7C is a pictorial representation illustrating Hoechst staining of example aligned microtissue in accordance with the examples of this disclosure. The mesoscale tissues (See FIGS. 7A, 7B, & 7C) were large enough to be handled using forceps and a scalpel, or by pipetting. The gut SMCs that matured as tissues within hydrogels are capable of aligning and generating force under stimulation.

Examples of the present disclosure disclose that the aligned microtissues may have significantly greater nuclear alignment than non-aligned control. In some examples, no difference in cell viability or proliferation between groups are realized at this stage, due to the small size of the microtissues. In other examples, it may be demonstrated that heSMCs may be formed into highly aligned microtissues through strain induction. In some examples, after 7 days of culture, both the aligned microtissue and non-aligned control groups may tend towards a contractile phenotype, but that the aligned microtissue group may have a higher total SM-MHC expression per cell than the non-aligned control. Additionally, the aligned microtissue may have the greatest expression of Connexin 43 (is a protein that is a component of gap junctions, which allow for gap junction intercellular communication between cells to regulate cell death, proliferation, and differentiation). This may provide insight into the phenotype switching of heSMCs related to cell alignment.

In the following examples, aligned bioprinting and force generation from macroscopic tissues may be discussed. Pre-aligned microtissues may be suspended in a bio-ink made of 5% GelMA (gelatin methacryloyl (GelMA) is a versatile material for a wide range of bioapplications) with 50 mg/mL Lithium phenyl-2,4,6-trimethylbenzoyl phosphinate (LAP) photoinitiator. Parallel lines may be printed into a culture dish to make an aligned tissue, then crosslinked with 405 nm light. To assess microtissue alignment immediately after printing, specimens may be fixed and embedded in paraffin for sectioning and optical microscopy. The angle between the long axis of the microtissues and the long axis of the printed specimen may be measured. The goal may be to have 90% of the microtissues with alignment angles below 10°, demonstrating that the pre-aligned microtissues are themselves aligned with the printing direction. Long-term cellular alignment after printing may be assessed by culturing the tissues for 14 days, then obtaining paraffin-embedded sections and quantifying the nuclear angles of the cells. These measurements may be compared to a control group where heSMCs are suspended as individual, free-floating cells in a 5% GelMA bio-ink. After 14 days of maturation in a petri dish, tensile testing may determine the material properties of the printed microtissue constructs.

In one example, the two ends of the microtissues may be attached to separate tissue grips on a Mach-1 mechanical tester (e.g., manufactured by Biomomentum located in Laval Canada). The microtissues may then be pulled to failure. The elastic modulus, ultimate failure stress, and ultimate failure strain may be measured. These values may be compared to non-aligned heSMC controls, to acellular, photo-crosslinked 5% GelMA controls, and to literature values for esophageal muscle tissue. Active force generation from the printed microtissues may be assessed by acetylcholine (ACh) stimulation and by electrical field stimulation in a dose-response manner. After 14 days of maturation, the specimens may be suspended between tissue grips on a tensile testing apparatus and pre-loaded to increasing lengths and stimulated with ACh and alternating current (AC) fields to determine force-length relationships.

Figure 8A:
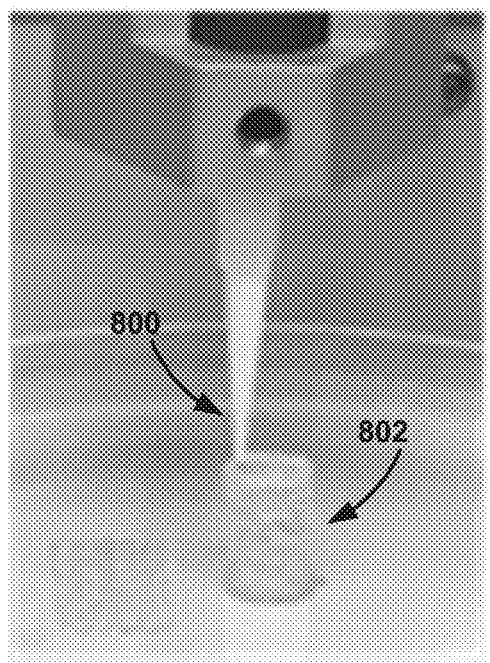
FIG. 8A is a pictorial representation of an example technique using 3D-printed model GelMA as conduit in accordance with examples of this disclosure.
Figure 8B:
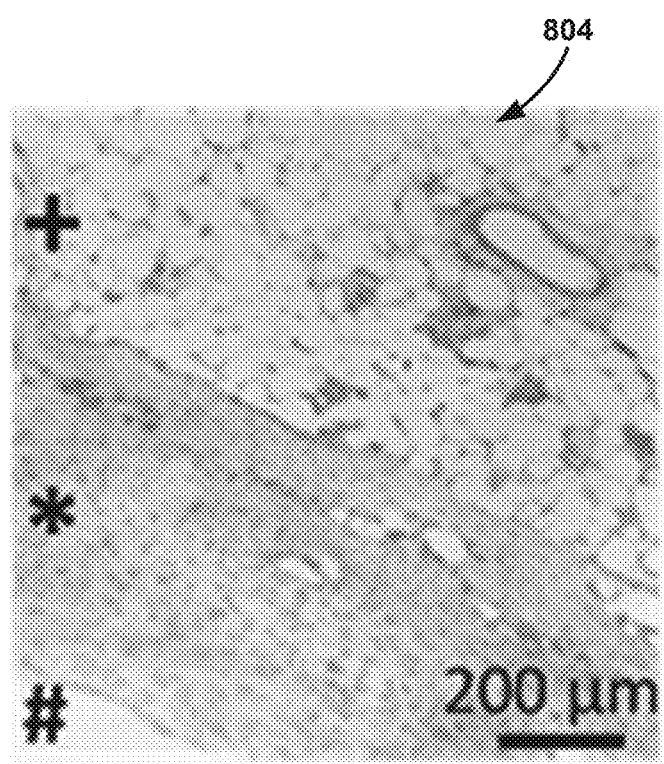
FIG. 8B is a pictorial representation of an example lumen and conduit post 6-week maturation where #is a lumen, * is a remodeled conduit, + is a greater omentum in accordance with examples of this disclosure.

FIGS. 8A and 8B are pictorial representations of an example technique using 3D-printed model GelMA 804 as conduit and an example lumen and conduit post 6-wk maturation where # is a lumen, * is a remodeled conduit, + is a greater omentum in accordance with examples of this disclosure. In another example, GelMA 804 may be a potential bioprinting ink for esophageal and GEJ tissue-engineering and it may be easily printed into a variety of geometries. In examples of the present disclosure, printed acellular GelMA conduits 802 from nozzle 800 (See FIG. 8A) may be implanted in the greater omentum of New Zealand White rabbits, demonstrating in vivo remodeling and remodeling of the GelMA. After 6 weeks, the conduit was remodeled, densely populated, and vascularized by host cells (See FIG. 8B).

Figure 9A:
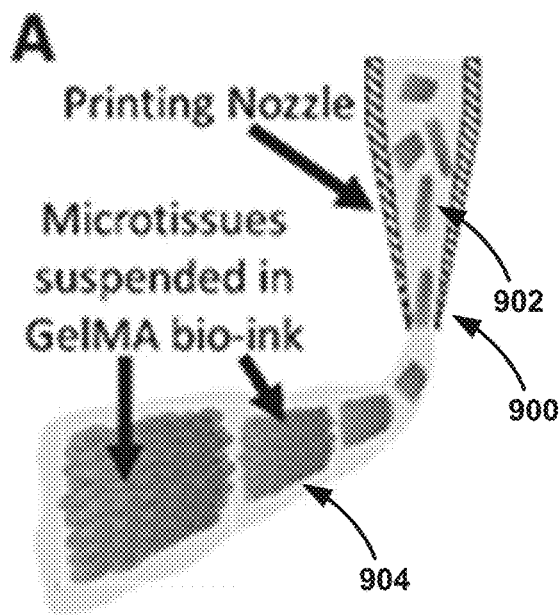
FIG. 9A is a graphical representation illustrating an example microtissue printing method in accordance with examples of this disclosure.
Figure 9B:
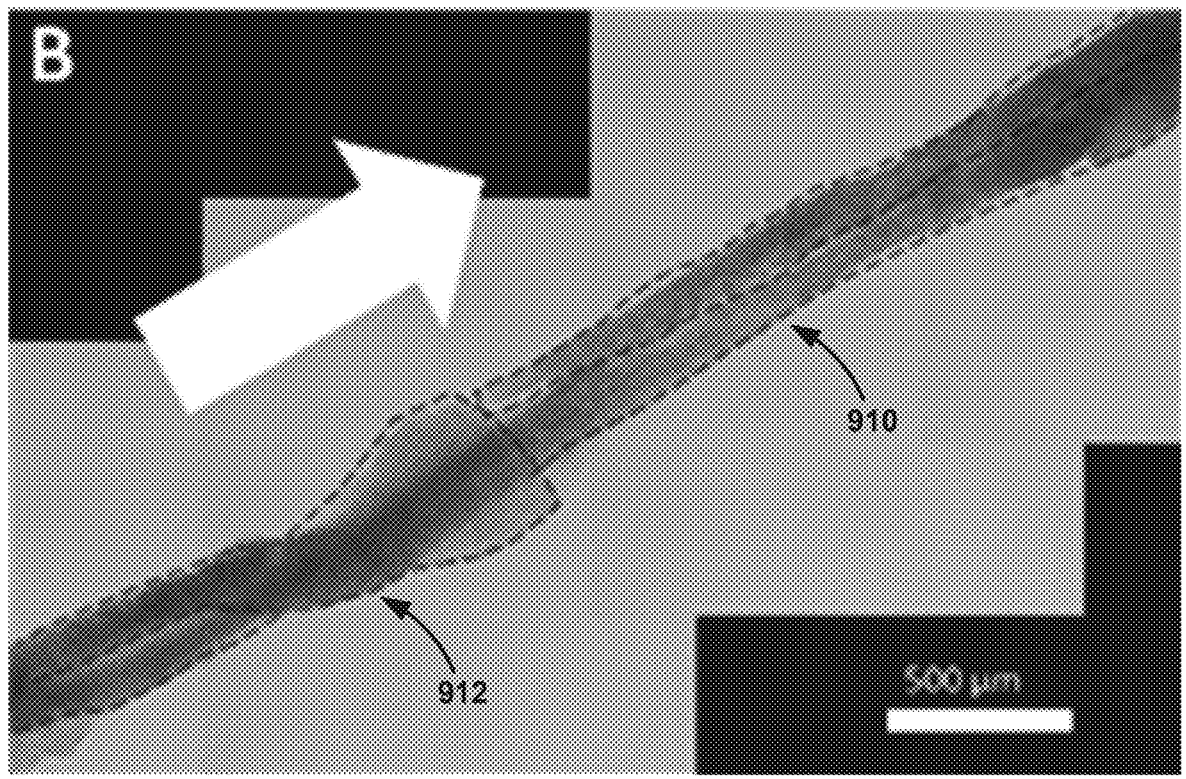
FIG. 9B is a pictorial representation illustrating an example single printed line of aligned, entangled mesoscale tissue strands in an example where the arrow shows a printing direction and individual strands are highlighted with dashed lines in accordance with examples of the disclosure.

FIGS. 9A and 9B are a pictorial representation illustrating an example microtissue printing method and an example single printed line of aligned, entangled mesoscale tissue strands in an alternative strategy where the arrow shows a printing direction and individual strands are highlighted with dashed lines in accordance with examples of the disclosure. Pre-aligned microtissues 902 are suspended in bio-ink until released from nozzle 900. For aligned tissue bioprinting, pre-aligned mesoscale tissues 904 (e.g., diameter 250 µm, length 1 cm) may be aligned in the printing direction when printed from printing nozzle 900 as a suspension in GelMA bioink (See FIG. 9B). The long tissue strands 910 and 912 may become entangled but were still aligned with the printing direction, or the direction in which the bioink flows out of the nozzle. In general, the pre-aligned microtissues may be created to have a length longer than the width. For example, the length to width ratio may be approximately 3:1 or greater. Such a length to width ratio may promote end-first delivery of the microtissues out of the nozzle. In some examples, the nozzle orifice may be selected to have a diameter sized to promote end-first exiting of the microtissues. For example, the nozzle may have an orifice diameter no greater than two times the diameter, or width, or the microtissues. In one example, the orifice diameter to microtissue diameter ration may be between 2:1 and 1.05:1.00. In another example, the orifice diameter to microtissue diameter ration may be between 1.5:1.0 and 1.1:1.0. This relatively small orifice size with respect to microtissue width may reduce the likelihood that any microtissues exit the nozzle without the end of the microtissue exiting first. Put another way, the microtissues will generally align with the flow of bioink and exit the nozzle in in the same direction of the pre-aligned cells of the microtissue.

In examples of the present disclosure, the printed microtissue group may have significantly greater alignment than the non-aligned printed group after 14 days of culture. This alignment may lead to greater force output from the printed microtissue group versus the non-aligned control group when stimulated by ACh or by an AC electrical field. End-to-end pre-aligned microtissue printing provides improved aligned tissues with greater force generation than traditional bioprinting.

Examples of the present disclosure demonstrate the ability to make the microtissues. In contrast to traditional methods where the short microtissues may not maintain their alignment. A meso-scale method for printing as demonstrated above may be used. Microtissues may be printed into more complicated geometries with this meso-scale approach to printing. In traditional methods, during maturation of the printed tissues, the heSMCs show decreased proliferation if they are more of a synthetic phenotype in the microtissue. This may be addressed by supplementation of individually suspended heSMCs, that have high proliferative capacity and may "fill the gap" between microtissues. While it is possible the tissues may not be contractile enough to measure, this outcome is unlikely as gut SMCs ability to form contractile tissue in hydrogels has been demonstrated. Histological evaluations demonstrating alignment may be beneficial to other fields of tissue engineering as there is value in aligning non-contractile tissues as well. Maintaining the contractile phenotype may be beneficial.

Printing of a tissue with pre-vascularized microtissue bio-ink may result in faster development of capillary networks compared to traditional individually suspended cell bioprinting. While pre-vascularization of microtissues has been accomplished in the context of spheroids but has not been applied in 3D bioprinting smooth muscle. Capillary tube formation may be demonstrated using multiple stromal and endothelial cell types. In examples of the present disclosure, pre-vascularized spheroids using heSMCs and human umbilical vein endothelial cells (hUVECs) may be developed. HUVECs are a widely used model cell type for endothelial cell experiments, and readily form capillary networks in 3D culture. Although pre-vascularized spheroids have been made previously, heSMCs have not yet been used.

Figure 10A:
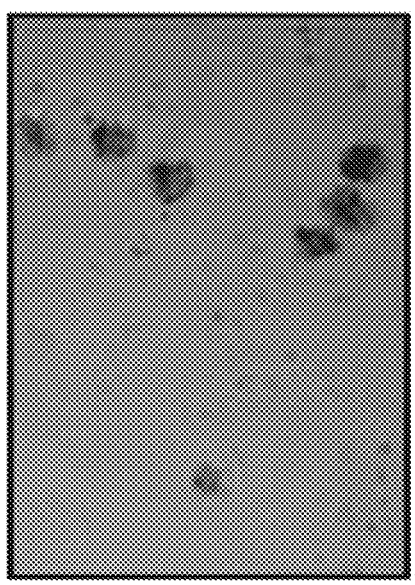
FIG. 10A is a pictorial representation of an example of sprouting of heSMC and hUVEC spheroids in collagen gel with a cell ration of 1:0 at zero hour in accordance with examples of this disclosure.
Figure 10B:
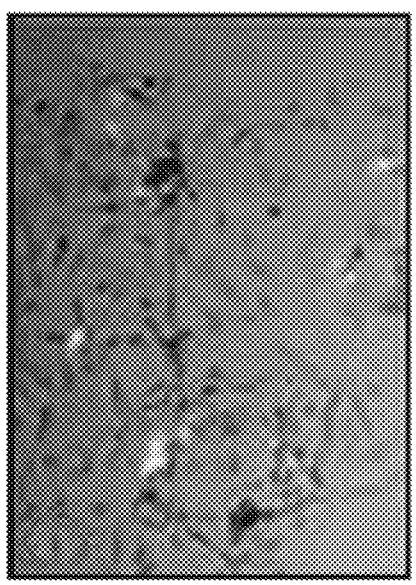
FIG. 10B is a pictorial representation of an example of sprouting of heSMC and hUVEC spheroids in collagen gel with a cell ration of 9:1 at zero hour in accordance with examples of this disclosure.
Figure 10C:
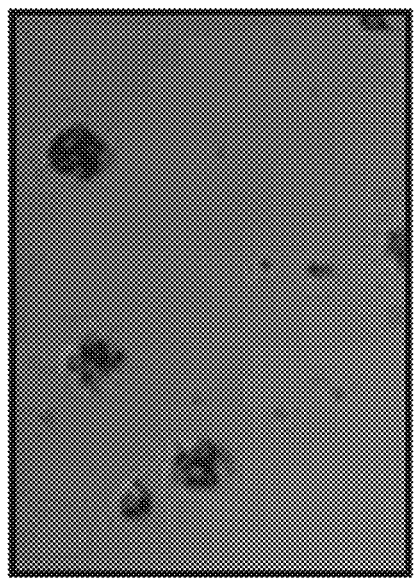
FIG. 10C is a pictorial representation of an example of sprouting of heSMC and hUVEC spheroids in collagen gel with a cell ration of 1:1 at zero hour in accordance with examples of this disclosure.

FIG. 10A is a pictorial representation of an example of sprouting of heSMC and hUVEC spheroids in collagen gel with a cell ration of 1:0 at zero hour in accordance with examples of this disclosure. Pre-vascularized microtissues may be produced as spheroids by culturing heSMCs and hUVECs in a specialized microwell plate (e.g., Aggrewell™ 400, manufactured by STEMCELL™ Technologies located in Vancover British Columbia). HUVECS expressing red fluorescent protein (RFP$^+$; Angio-Proteomie) may be used, allowing for live monitoring of tissue maturation. The ability of these pre-vascularized spheroids to form capillary sprouts outside of the spheroid may be assessed by embedding them sparsely in a larger acellular hydrogel. Prior to embedding, the spheroids may be incubated in Qtracker™ 525 cell labeling solution (manufactured by Thermo Fischer Scientific located in Waltham, Massachusetts), allowing easy visualization within the acellular gel. Cellular sprouting outward into the gel that is positive for both the green cell tracker and RFP may be quantified for sprout number and length. Examples of the present disclosure may use a mixed factorial experimental design to choose the best ratios of cells, total cell number, and culture medium mixing ratios (See Table 1). Spheroid diameter may be monitored throughout culture by microscopy, with a goal diameter of 200±20 µm for future bioprinting work. Key outcomes for these experiments may be assessed by confocal microscopy and microplate assays.

TABLE 1

Levels for mixed factorial design

| Parameter | Level 1 | Level 2 | Level 3 | Level 4 |
| --- | --- | --- | --- | --- |
| Total Cells Per Microtissue | 50 | 100 | 200 | |
| heSMCs:hUVECs | heSMCs | 10:1 | 1:1 | hUVECs |
| SMC medium: EC medium | SMC medium | 1:1 | EC medium | |

Figure 10D:
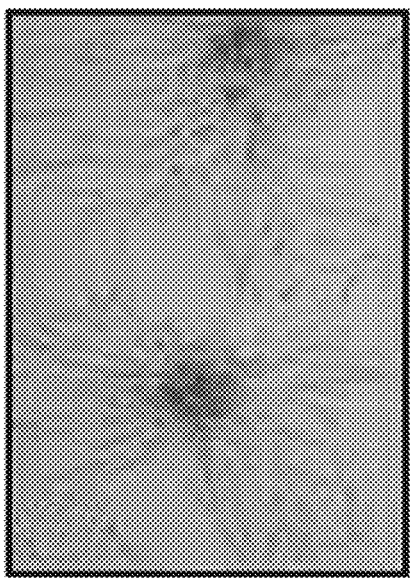
FIG. 10D is a pictorial representation of an example of sprouting of heSMC and hUVEC spheroids in collagen gel with a cell ration of 0:1 at zero hour in accordance with examples of this disclosure.
Figure 10E:
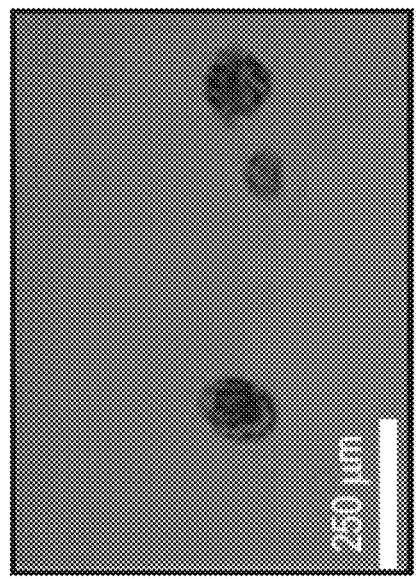
FIG. 10E is a pictorial representation of an example of sprouting of heSMC and hUVEC spheroids in collagen gel with a cell ration of 1:0 at twenty-four hours in accordance with examples of this disclosure.
Figure 10F:
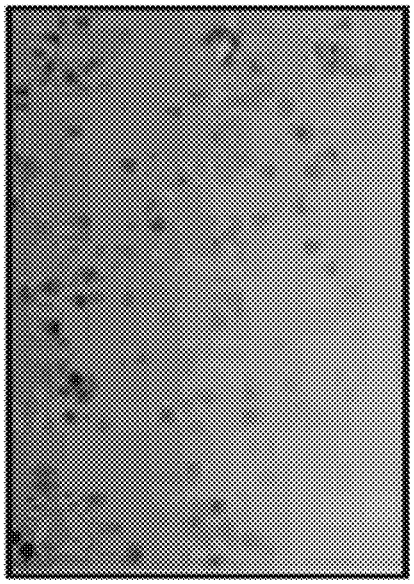
FIG. 10F is a pictorial representation of an example of sprouting of heSMC and hUVEC spheroids in collagen gel with a cell ration of 9:1 at twenty-four hours in accordance with examples of this disclosure.
Figure 10H:
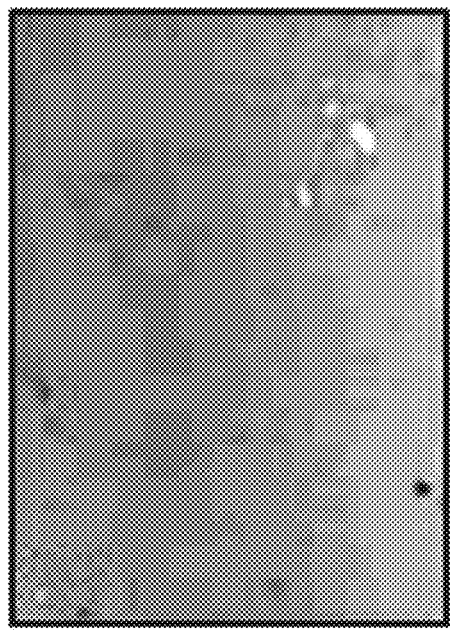
FIG. 10H is a pictorial representation of an example of sprouting of heSMC and hUVEC spheroids in collagen gel with a cell ration of 0:1 at twenty-four hours in accordance with examples of this disclosure.
Figure 10G:
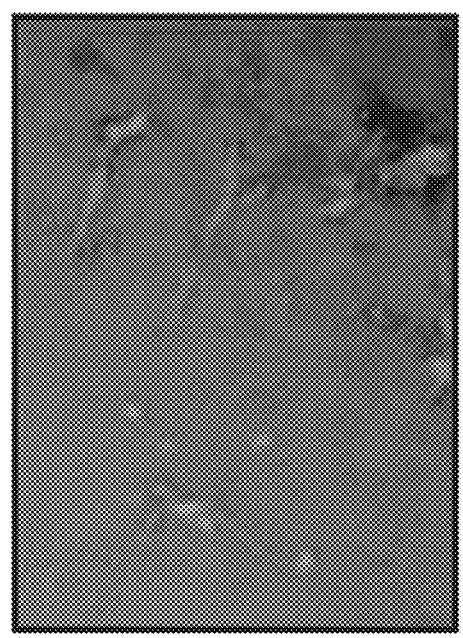
FIG. 10G is a pictorial representation of an example of sprouting of heSMC and hUVEC spheroids in collagen gel with a cell ration of 1:1 at twenty-four hours in accordance with examples of this disclosure.

Examples of the present disclosure have demonstrated that heSMCs and hUVECs may be co-cultured to form spheroids of various cell ratios within 48 hours. When embedded in collagen gels, smooth muscle-only spheroids demonstrated robust outgrowth (See FIGS. 10A, 10E). Red fluorescent protein (RFP$^+$) hUVECs mixed with heSMCs (FIGS. 10B, 10C, 10F, 10G) demonstrated sprouting after only 24 hr. HUVEC-only spheroids are mechanically weak and broke apart during pipetting (FIG. 10D). The dissociated cells still show sprouting potential (FIG. 10H). Examples of the present disclosure show there exists an heSMC:hUVEC ratio and a smooth muscle medium: endothelial cell medium ratio that maximizes endothelial sprouting.

Figure 11A:
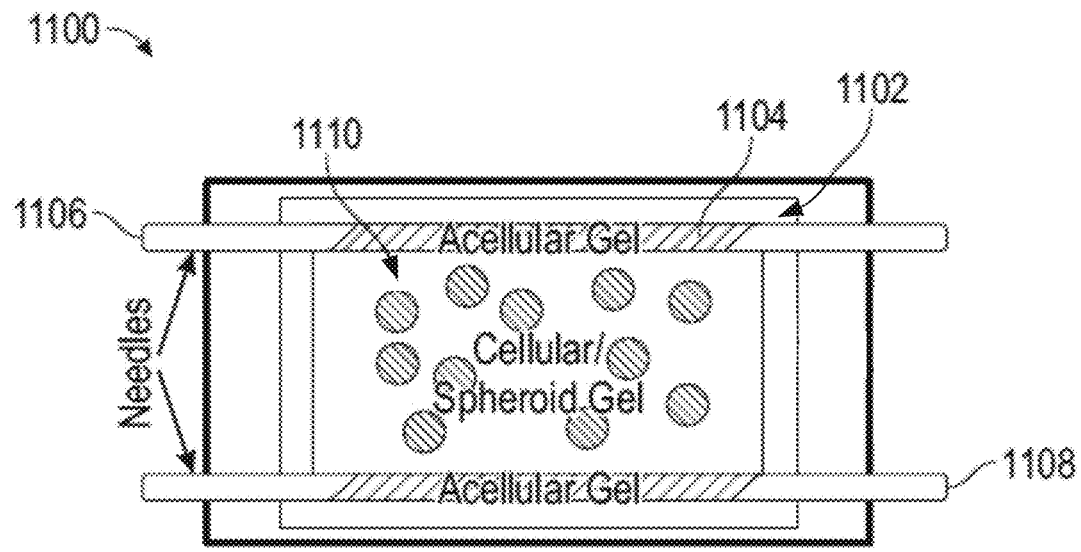
FIG. 11A is a graphical representation of an example initial configuration of a vascularization device in accordance with examples of this disclosure.
Figure 11B:
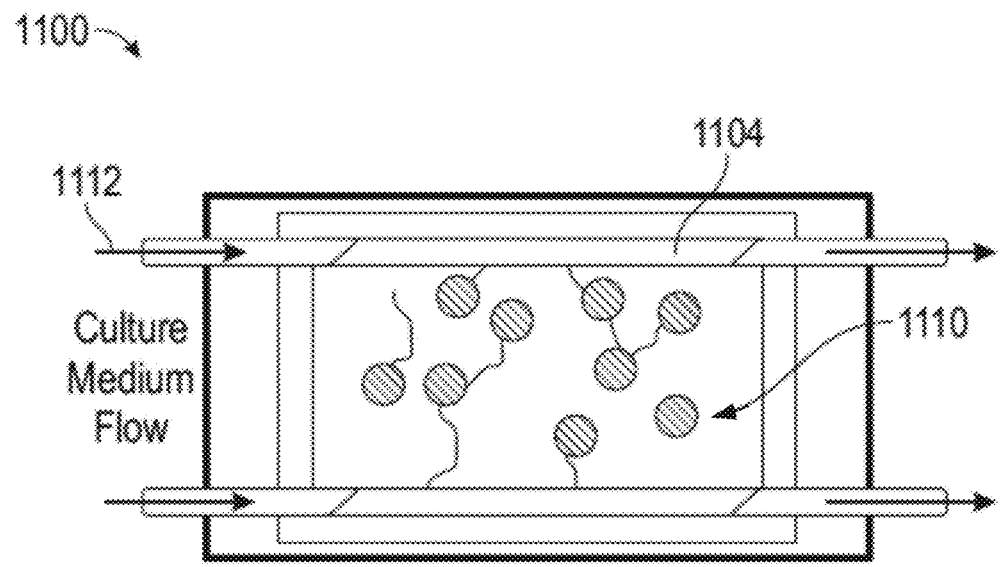
FIG. 11B is a graphical representation of an example vascularization device after washing out channels and maturating capillary networks in accordance with examples of this disclosure.

FIGS. 11A and 11B are graphical representations of an example initial configuration of a vascularization device 1100 in accordance with examples of this disclosure. Vascularization device 1110 may include silicone border 1102, lines of gelatin 1104, input needles 1106, output needles 1108, and bioink gel 1110. Examples of the present disclosure may use a modified capillary formation assay to assess traditional methods. A glass slide may be prepared with a square outline made from silicone to create silicone border 1102. Two parallel lines of acellular 10% gelatin 1104 (not methacrylated) may be bioprinted at room temperature on the inner sides of these silicone lines 1104. A pre-vascularized bio-ink 1110 made of the vascularized microtissues and 5% GelMA (with LAP) may be printed between these acellular 10% gelatin lines 1104 onto the glass slide. Finally, a glass coverslip may be laid on top of the device, completely encasing the device 1100 in silicone and glass. Four small needles (e.g., input needles 1106 and output needles 1108) may be inserted through the silicone border 1102 sidewalls at the ends of the acellular gelatin lines 1104 (See FIG. 11A). The exposure to 405 nm light may crosslink the GelMA central region 1110, then incubated at 37° C. to liquify the non-methacrylated gelatin that may be washed away through the output needles 1108 (See FIG. 11B) using culture medium 1112 flowing through input needles 1106. Additional hUVECs may be seeded into the printed channels to form an endothelial lining. Device 1100 may be placed in an incubator and perfused with a peristaltic pump (not shown).

Capillary formation may be assessed every 2 days for 14 days by microscopy, quantifying capillary branching and length as shown by RFP+ hUVECs. The pre-vascularized microtissue bio-ink may be compared to a traditional bioprinting control where hUVECS and heSMCs are freely suspended, rather than formed into microtissues. Other controls may be heSMC-only bio-ink and acellular bio-ink. At days 7 and 14, capillary flow may be assessed by adding 150 kDa Fluorescein isothiocyanate (FITC)-dextran to one side of the device and obtaining pictures every 2 minutes using an EVOS FL Auto 2 Cell Imaging System (manufactured by Invitrogen™) automated microscopy, then calculating the diffusional permeability of the specimen.

Figure 12B:
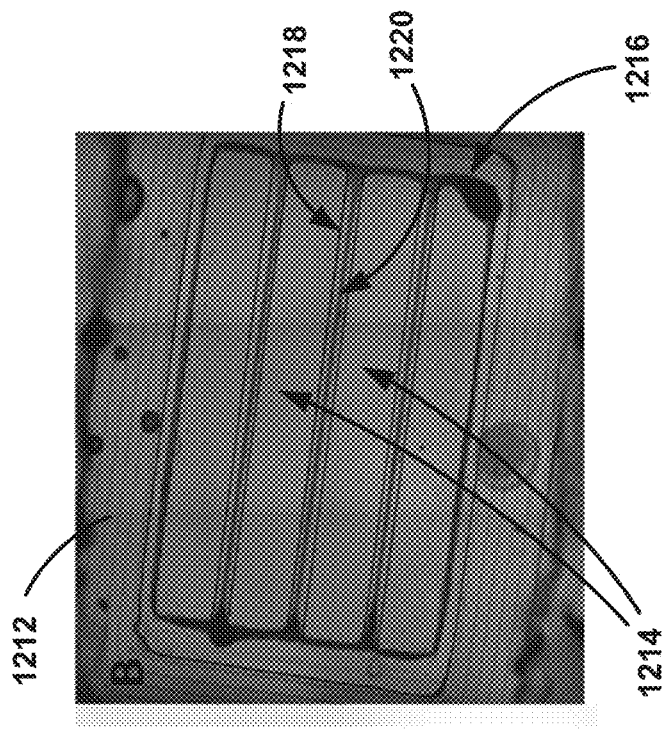
FIGS. 12A and 12B are example molds for generating microtissues having cells aligned in one direction in accordance with examples of this disclosure.
Figure 12A:
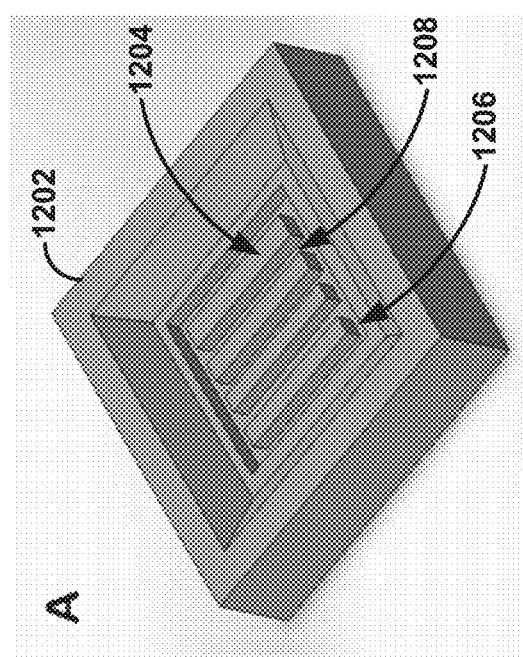

FIGS. 12A and 12B are example molds for generating microtissues having cells aligned in one direction in accordance with examples of this disclosure. Microtissues may be formed to include cells aligned in a single direction using any number of structures, such as posts, grooves, or wells that may constrain cells to alignment in a single direction. As shown in FIG. 12A, mold 1202 is designed to include channels 1208 formed between walls 1204, and mold 1202 may be referred to as a "harp mold" in some examples. In this manner, walls 1204 divide mold 1202 into the different channels 1208, where a single microtissue can form within a respective channel 1208. End gap 1206 enables the ends of walls 1204 to constrain the contraction of gel and tissues within the gel. In this manner, the ends of walls 1204 may act as attachment structures that retain tissue to constrain the cells in a single direction along the channel 1208. Once the cells are matured, an operator can cut the microtissues free using a sharp instrument (e.g., a razor). In some examples, the ends of each microtissue can be discarded because the main purpose is to hold the developing microtissues in place within each of channels 1208. As shown in FIG. 12B, mold 1212 is similar to mold 1202. Cells in a collagen solution can be centrifuged into mold 1212, and then the excess fluid is aspirated. As the cells remodel and compact the gel, tension develops along the members and alignment is induced, as is shown in microtissue 1220 (e.g., pre-aligned microtissue that includes smooth muscle cells after maturation). Microtissue 1220 has been generated within channel 1218 between adjacent walls 1214. An operator can remove microtissue 1220 from the adjoining tissue that has formed in end gap 1206.

Examples of the present disclosure disclose that the bio-ink made from pre-vascularized heSMC microtissues may develop capillaries more quickly than any of the controls that may be demonstrated by microscopy and by an increased dextran permeability at both day 7 and day 14. Fibroblasts may be used instead of heSMCs as a second cell type co-seeded with hUVECS. If angiogenesis is poor, pro-angiogenic molecule gradients such as vascular endothelial growth factor may be used to induce network formation. Addition of vascular pericyte cells such as mesenchymal stem/stromal cells may also enhance angiogenesis. Finally, if the GelMA bioink does not yield optimal results, a fibrin-based ink may be used.

Figure 13B:
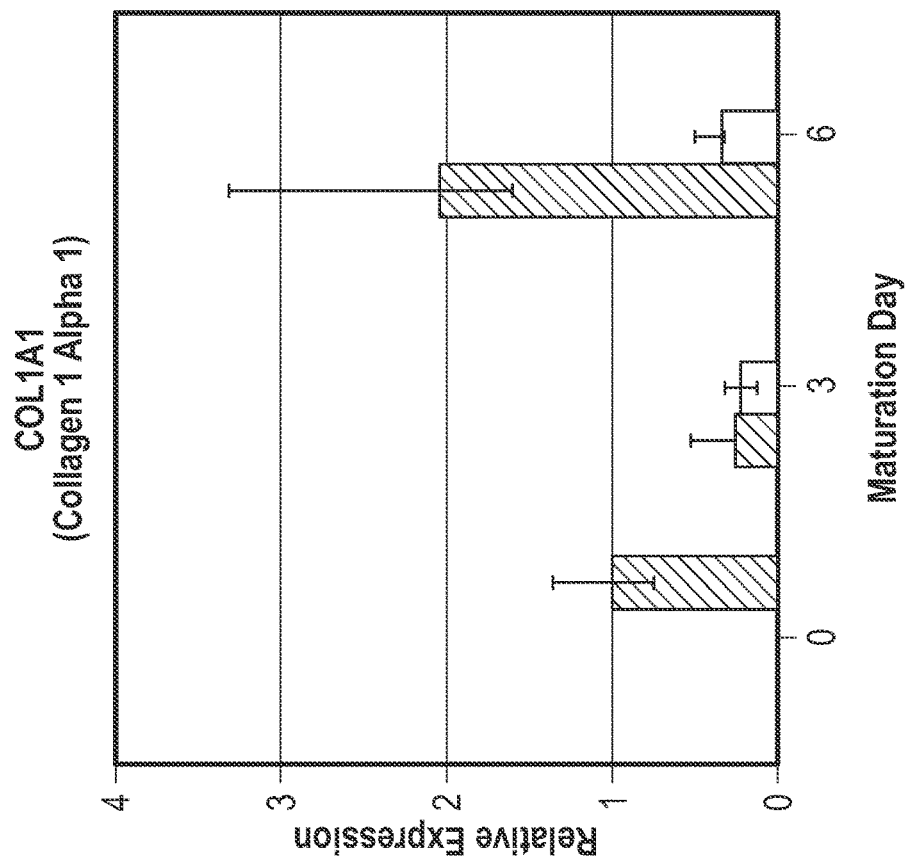
FIGS. 13A and 13B are example graphs of actin and collagen developed in aligned and unaligned environments.
Figure 13A:
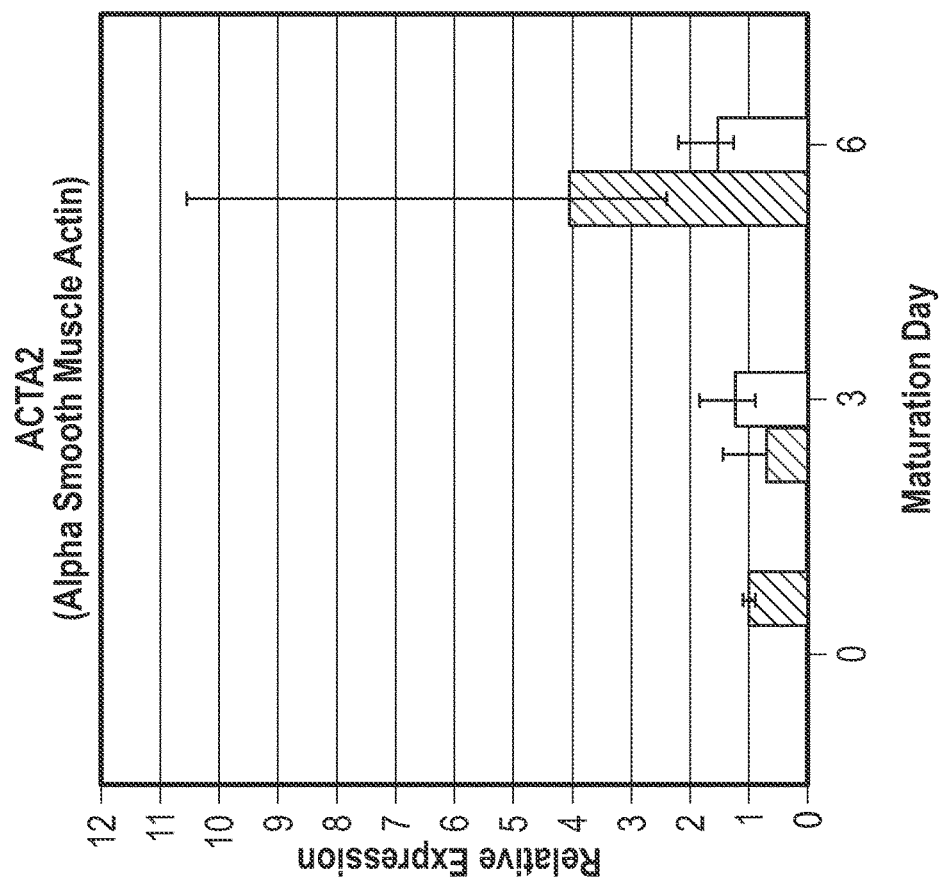

FIGS. 13A and 13B are example graphs of actin and collagen developed in aligned and unaligned environments. In general, FIGS. 13A and 13B provide evidence that esophageal smooth muscle cells are positively influenced by being in an aligned microtissue environment compared to an unaligned environment. As shown in FIG. 13A, the amount of smooth muscle actin mRNA, which corresponds with the ability of cells to generate contraction force, was increased over the course of 6 days, as shown in the left bars for days 3 and 6. In comparison, actin from cells in an unaligned microtissues, as shown in the right bars for days 3 and 6 did not significantly increase contraction force. Likewise, as shown in FIG. 13B, the cells produced a greater amount of mRNA for collagen 1 protein (as shown by the left bars for days 3 and 6 indicative of 3D aligned microtissues, where the right bars for days 3 and 6 are indicative of unaligned microtissues), which is an indicator that the cells are actively remodeling their environment and creating more extracellular matrix to strengthen the tissue. In other words, pre-aligning microtissues as described herein can generate a more mature cell for use in printing larger cellular structures than if the cells were allowed to align on their own after printing.

The results in FIGS. 13A and 13B demonstrate that the aligned microtissues themselves are more like normal smooth muscle tissue than unaligned tissues. This supports the premise that pre-aligning or pre-maturing microtissues leads to better overall tissue quality when compared to unaligned microtissues. When the microtissues are assembled, they will impart this enhanced tissue quality and cellular function to the larger assembly. Furthermore, this demonstrates a unique new point in process control for tissue engineering. Rather than simply performing quality control tests on the beginning ingredients (e.g. cells and hydrogel components) and the final product, this additional set of quality control tests can be performed at this intermediate step. This test can allow for a greater amount of control over the tissue engineering process, as batches of microtissues can be screened for desired attributes before moving into the next step of assembly into the final large tissue.

Figure 14A:
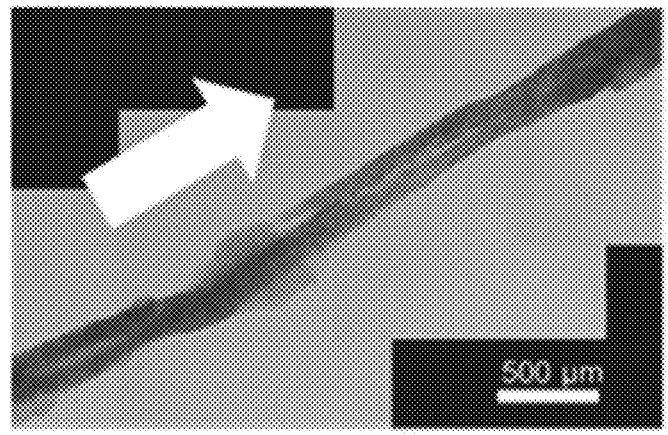
FIG. 14A and 14B illustrate example structures printed using pre-aligned microtissues.
Figure 14B:
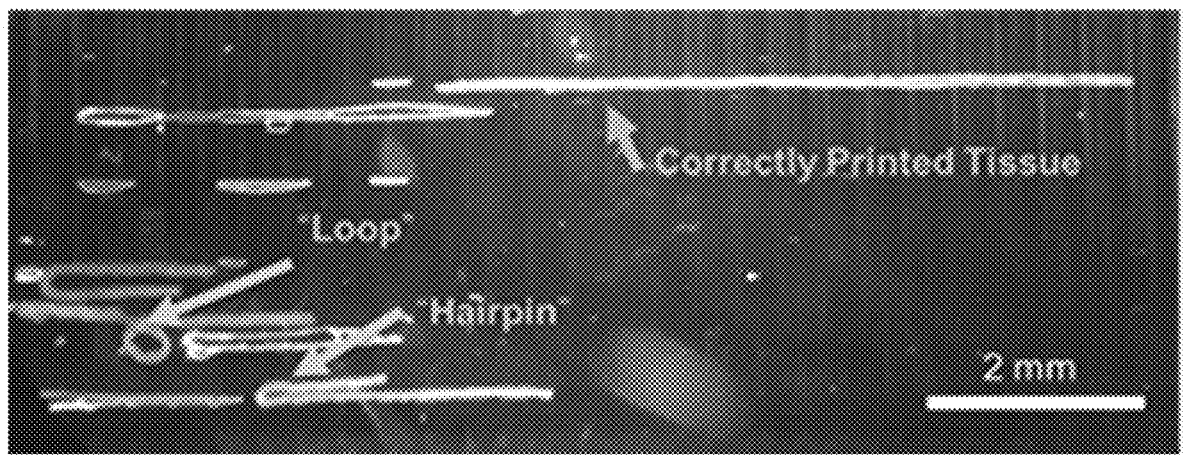

FIGS. 14A and 14B illustrate example structures printed using pre-aligned microtissues. The long, aligned microtissues shown can be printed into larger structures in which the microtissues themselves are also aligned, as demonstrated in the pre-aligned microtissues aligned in the direction of the arrow in FIG. 14A. There are possible "error states" for the printing process. Some of the microtissues may become folded or looped prior to extrusion through the printing nozzle. These folded or looped microtissues can lead to "hairpins" or "loops" in the printed construct as shown in FIG. 14B. The system can reduce these potential errors by adjusting tissue length and printing flow characteristics. For example, slower printing speeds may reduce folding of tissues. In another example, a nozzle with a diameter larger than the diameter of the pre-aligned microtissue and smaller than two times the diameter of the pre-aligned microtissue can reduce this folding of microtissues from flowing out of the nozzle in this error form. A nozzle orifice diameter closer to the diameter of the microtissues to be printed may further limit folding during printing. However, even in the presence of such errors, a large majority of the microtissues can still be aligned in the desired direction as printed from the nozzle.

Figure 15B:
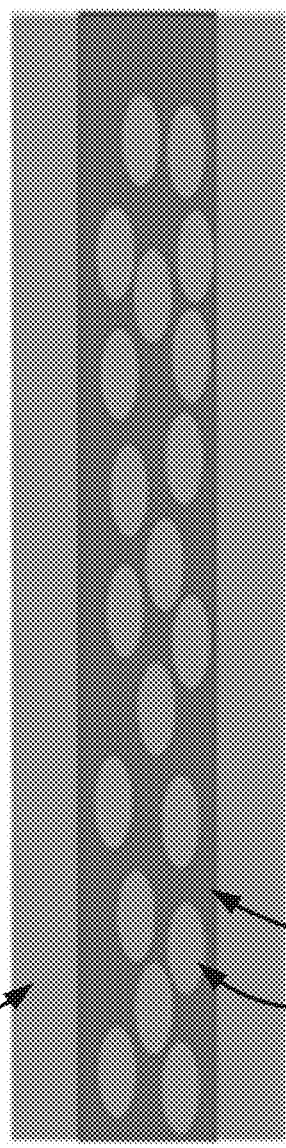
FIGS. 15A, 15B, and 15C are example cross-section and profile views of example fibers generated using a core-shell spinning technique.
Figure 15C:
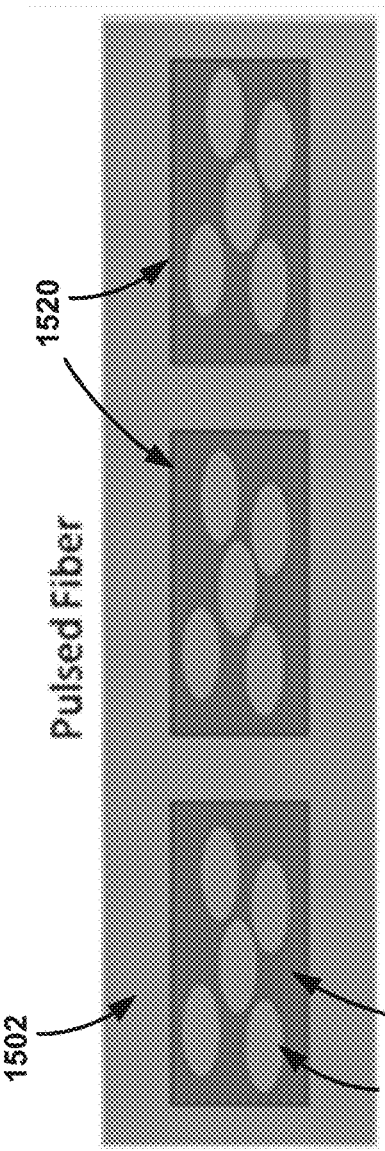
Figure 15A:
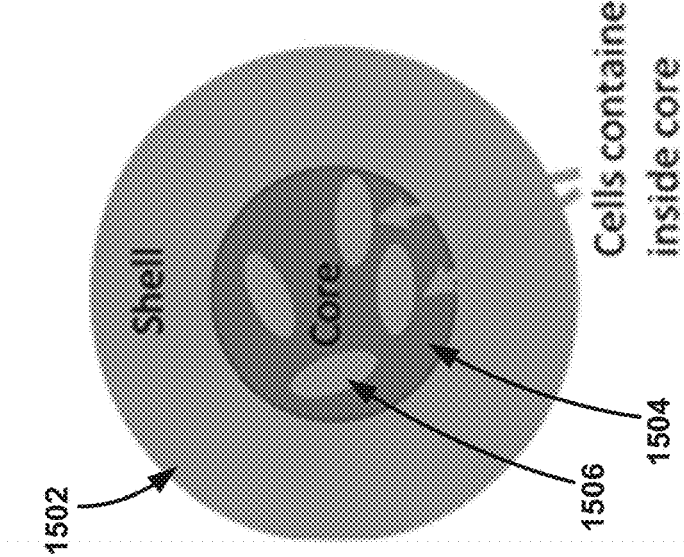

FIGS. 15A, 15B, and 15C are example cross-section and profile views of example fibers generated using a core-shell spinning technique. One example process for microtissue formation involves a casting process. For example, hydrogels and cells can be cast into a mold and allowed to mature and contract to form the pre-aligned microtissues. This casting process can take more time and reduce throughput of microtissues compared to other production techniques. For example, a different method of production of pre-aligned microtissues may utilize a core-shell wet spinning approach. This process of co-axial or core-shell spinning can produce very long fibers made from cells 1506 and a hydrogel 1504, within shell 1502. In this core-shell approach, cells 1506 can proliferate and exert contractile force in hydrogel 1504, which leads to alignment of cells 1506 along the complete fiber direction (e.g., in the direction parallel with a longitudinal axis of the fiber. The material of shell 1502 can be dissolved away after maturation, leaving only the core cellular fiber behind, which include cells 1506 as part of pre-aligned microtissues.

The technique can use the wet spinning method to create long fibers or microtissues which will then be divided into smaller tissues and collected for use in bioprinting. For example, wet spinning can produce a continuous fiber which is then be cut into smaller pieces. In another example, these smaller pieces may be formed into a "pulsed fiber" as shown in FIG. 15C which would compartmentalize small pieces of cellular core material (e.g., cells 1506 and hydrogel 1504) into discrete microtissue units 1520. Rather than cutting a long fiber into smaller fibers, the technique can simply dissolve away the material of shell 1502 in order to expose the individual microtissue units 1520 for collection and printing.

In one example, the technique may use alginate as a shell material, which encases a core of cells and collagen or some other pre-gel solution. After maturation of the cells and collagen into a microtissue, the technique may involve dissolving the alginate shell material by chelation of calcium ions or by an alginate degrading enzyme such as alginase. Microtissues can be produced as short lengths (lengths between approximately 200-500 microns and length to width aspect ratios between approximately 2:1-5:1), allowing for high printing resolution and small curvature radius during the following bioprinting process. Microtissues can also be produced as longer segments (lengths between approximately 500-2000 microns) and a high aspect ratio (e.g., length to width aspect ratios of 5:1-20:1), which may enable better physical entanglement and strength of any tissues printed with these microtissues. This process may enable a system to generate discrete and repeatable microtissue units 1520 in a very rapid manner.

Figure 16A:
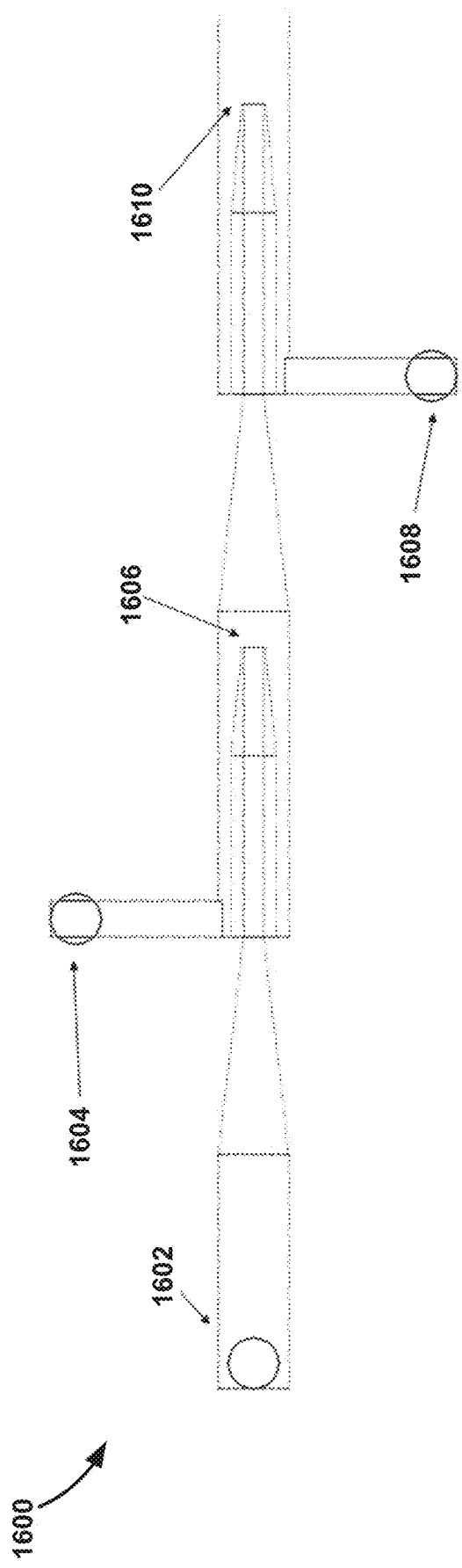
FIGS. 16A and 16B are conceptual diagrams of an example spinning device for generating microtissue structures.
Figure 16B:
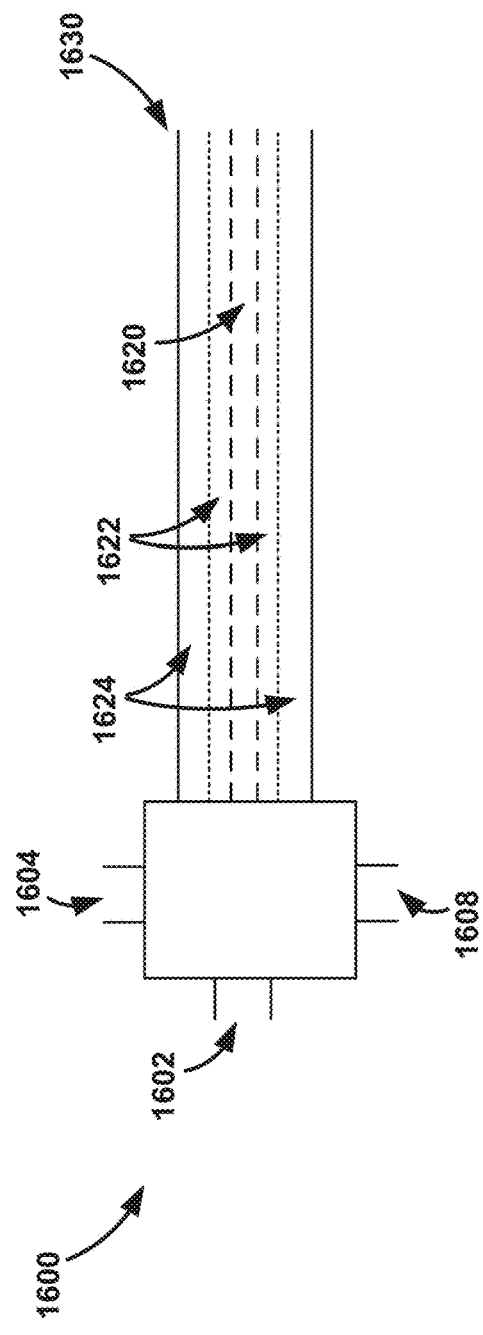

FIGS. 16A and 16B are conceptual diagrams of an example spinning device 1600 for wet spinning microtissues such as the fibers and microtissue units 1520 of FIGS. 15A, 15B, and 15C. Spinning device 1600 can control the size of the core fiber by controlling the flow rates of the material (e.g., shell material, cells, and hydrogel, through spinning device 1600. The microtissue units generated by spinning device 1600 can be loaded into a printer and deposited by the bioprinter in a non-continuous manner, which is the approach required for many complicated structures like the heart, gastroesophageal junction, etc. For example, these small microtissues can later be assembled into larger tissues by bioprinting to exert much more control over the quality and character of the final product.

As shown in the example of FIG. 16A, spinning device 1600 includes three different inlets, core stream inlet 1602, shell stream inlet 1604, and sheath stream inlet 1608. Each of these inlets injects material to form a respective portion of microtissue. Cells and the core material is injected first through core stream inlet 1602. Then, the shell material is added through shell stream inlet 1604 and added circumferentially around the core (e.g., at locations radially outward from the core) via spinneret 1606. This combined material may be referred to as the microtissue fiber or units. Then, sheath material is added through sheath stream inlet 1608 and added to the outside of the microtissue from spinneret 1606 via spinneret 1610 to create the output material that includes the microtissue that can be printed.

In this manner, spinning device 1600 can use a series of coaxial nozzles or spinnerets (e.g., spinnerets 1606 and 1610) to layer the shell material over the core that includes the cells to be pre-aligned within the shell. For example, spinneret 1606 can inject a stream of core fluid into the center of a larger stream of shell fluid. Then, the coaxial fluid streams are injected through a second spinneret 1610 into the center of a larger stream of fluid (e.g., the sheath material) which can contain crosslinking chemicals to convert the coaxial core and shell streams into a solid fiber. In another example, all three streams can be introduced at the same point by a coaxial nozzle made of three independent nozzles of decreasing size inserted into each other.

The example of FIG. 16B illustrates a conceptual diagram of spinning device 1600. As shown, core stream inlet 1602, shell stream inlet 1604, and sheath stream inlet 1608 can converge within a fluid manifold that may take the form as shown in FIG. 16A or other fluid flow channels. Outlet material 1630 is shown as a cross-sectional view of the coaxial material and includes core stream 1620 in the middle, shell stream 1622 radially outward from core stream 1620, and sheath stream 1624 radially outward from shell stream 1622. In this manner, shell stream 1622 may depict the shell of the spun microtissue, which can provide structural support during development or pre-aligning of the cells. Core stream 1620 includes the core of the microtissue, which contains cells and a hydrogel material that develop into the aligned microtissue.

The flow rate of material out of spinning device 1600 may be varied based on cell size, hydrogel viscosity, or other factors. In one example, the flow rate may be between approximately 20 microliters per minute and 200 micro liters per minute. In another example, the flow rate may be between approximately 50 microliters per minute and 100 micro liters per minute. In an example at 50 microliters per minute, the shell stream 1624 may have a diameter of approximately 285 micrometers, and core stream 1622 may have a diameter of approximately 94 micrometers. In another example at 100 microliters per minute, the shell stream 1624 may have a diameter of approximately 316 micrometers, and core stream 1622 may have a diameter of approximately 173 micrometers. These example dimensions are merely for illustrative purposes, as other flow rates and dimensions are possible by using different characteristics of the material and spinner device 1600.

The microtissues described herein can be used with smooth muscle cells and other cells and tissues. In some examples, the pre-aligned microtissues may be used to create or build upon cardiac or skeletal muscle. In some examples, multiple types of microtissues can be printed simultaneously, such as to overlap or interdigitate fibers of skeletal muscle and tendon tissue which results in a strong bond between the two tissue types at various tissue type junctions. Creating strong musculotendinous junctions, for example, can be advantageous for treatment of sports injuries, battlefield injuries, and other high energy trauma to soft tissue or other tissues.

The microtissues described herein may be printed in different environments, such as building a larger construct in-vivo or in-vitro. In-vitro construct building may be done prior to implantation of that construct in a subject or otherwise used for a desired purpose. For in-vivo printing, the technique may involve directly printing pre-aligned microtissues to another native tissue. For example, the microtissues may be printed onto a native organ to fill a gap in muscle caused by disease or trauma. This new muscle fibers may repair a tear in muscle. This process could also be used for tendons, cardiac muscle, or any other tissue. The system may align the fibers of the printed microtissues with the fibers of the native tissue. In this manner, printing of the pre-aligned microtissues described herein may be performed to treat injury, repair damage, replace tissue, extend native tissue, or otherwise fix a defect in native subject tissue.

The following examples are described herein. Example 1: A method of printing a tissue construct, the method comprising aligning cells in a first direction to create pre-aligned microtissues; suspending the pre-aligned microtissues in a liquid to create a bioink; and depositing the pre-aligned microtissues in a second direction to create the tissue construct.

Example 2: The method of example 1, wherein aligning the cells in the first direction comprises: suspending, within one or more wells located on a substrate between a first attachment structure and a second attachment structure, the cells within a hydrogel; inducing, via compaction of the hydrogel, a strain on the cells to cause the cells to align in the first direction between the first attachment structure and the second attachment structure; and maturing, with bioreactor signals, the cells so that the cells are aligned in the first direction to create the pre-aligned microtissues.

Example 3: The method of any of examples 1 and 2, further comprising removing the pre-aligned microtissues from the first and second attachment structure prior to suspending the pre-aligned microtissues in the liquid to create the bioink.

Example 4: The method of any of examples 1 through 3, wherein depositing the pre-aligned microtissues in the second direction comprises 3D-printing, with a 3D bioprinter, the bioink including the pre-aligned microtissues into the tissue construct.

Example 5: The method of any of examples 1 through 4, further comprising maturing the tissue construct in a bioreactor.

Example 6: The method of any of examples 1 through 5, wherein the cells comprise muscle cells, and wherein the method further comprises: maturing the tissue construct of pre-aligned microtissues; and combining human umbilical vein endothelial cells (hUVECs) with the muscle cells to initiate vascularization of the tissue construct.

Example 7: The method of example 6, wherein the one or more muscle cells are gut smooth muscle cells (gSMC).

Example 8: The method of any of examples 1 through 7, wherein depositing the pre-aligned microtissues comprises depositing, through a nozzle, the bioink such that one pre-aligned microtissue of the pre-aligned microtissues pass through the nozzle at a time in an end-first orientation.

Example 9: The method of example 8, wherein depositing the pre-aligned microtissues comprises selecting a flow rate for the bioink through a narrowing passage of the nozzle such that the flow rate of the bioink through the narrowing passage of the nozzle aligns a longitudinal axis of the microtissues with a directional flow of bioink through the narrowing passage of the nozzle.

Example 10: The method of any of examples 1 through 9, wherein depositing the pre-aligned microtissues comprises depositing the pre-aligned microtissues on a scaffold.

Example 11: The method of example 8, wherein the nozzle comprises an orifice diameter from about 100 microns to about 200 microns.

Example 12: The method of any of examples 1 through 11, wherein the pre-aligned microtissues have a length to width ratio of at least 3:1.

Example 13: The method of any of examples 1 through 12, wherein depositing the pre-aligned microtissues in the second direction comprises printing the pre-aligned microtissues in a volume to create the tissue construct that comprises an anatomical connective tissue.

Example 14: A 3D-printed tissue construct comprising a plurality of pre-aligned microtissues, each pre-aligned microtissues comprising cells aligned in a first direction, wherein the plurality of pre-aligned microtissues deposited via a bioink in a second direction to form the 3D-printed tissue construct.

Example 15: The 3D-printed tissue construct of example 14, where in the cells comprise muscle cells, and wherein the 3D-printed tissue construct comprises one of a smooth muscle anatomical structure or a skeletal muscle anatomical structure.

Example 16: The 3D-printed tissue construct of any of examples 14 and 15, further comprising vascularization cells combined with the cells to initiate vascularization of the pre-aligned microtissues.

Example 17: The 3D-printed tissue construct of example 16, wherein the vascularization cells are human umbilical vein endothelial cells (hUVECs).

Example 18: The 3D-printed tissue construct of any of examples 14 through 17, wherein the cells comprise gut smooth muscle cells (gSMC).

Example 19: A system for printing a tissue construct, the system comprising a first bioreactor configured to mature and align cells in a first direction to create pre-aligned microtissues; a printer nozzle configured to deposit the pre-aligned microtissues in a second direction to create the tissue construct; and a second bioreactor to mature the tissue construct.

Example 20: The system of example 19, further comprising a substrate with one or more wells located between a first attachment structure and a second attachment structure, wherein the substrate is configured to suspend the cells within a hydrogel, and wherein, through compaction of the hydrogel, a strain on the cells cause the cells to align between the first and the second attachment structure in the first direction.

Examples of the disclosure may demonstrate pre-maturing microtissue building blocks for addressing muscle tissue alignment and vascularization. The examples may provide for rearranging the traditional process flow. In other examples, new methods for creating aligned and vascularized muscle that may be combined and used for further tissue engineering. Examples of the present disclosure discuss using long, pre-aligned microtissues that are suspended in a bio-ink and printed using a 3D extrusion bioprinter.

Various aspects of the disclosure have been described. These and other aspects are within the scope of the following claims.

What is claimed is:

1. A method of printing a tissue construct, the method comprising:
    aligning cells in a single direction to create pre-aligned microtissues with the cells aligned in the single direction;
    suspending the pre-aligned microtissues in a liquid to create a bioink comprising the pre-aligned microtissues; and
    dispensing the bioink out of a nozzle such that the pre-aligned microtissues exit the nozzle in a flow direction parallel with the single direction of cell alignment to create the tissue construct.

2. The method of claim 1, wherein aligning the cells in the single direction comprises:
    suspending, within one or more wells located on a substrate between a first attachment structure and a second attachment structure, the cells within a hydrogel;
    inducing, via compaction of the hydrogel, a strain on the cells to cause the cells to align in the single direction between the first attachment structure and the second attachment structure; and
    maturing, with bioreactor signals, the cells so that the cells are aligned in the single direction to create the pre-aligned microtissues.

3. The method of claim 1, further comprising removing the pre-aligned microtissues from the first and second attachment structure prior to suspending the pre-aligned microtissues in the liquid to create the bioink.

4. The method of claim 1, wherein dispensing the pre-aligned microtissues comprises 3D-printing, with a 3D bioprinter, the bioink including the pre-aligned microtissues into the tissue construct.

5. The method of claim 1, further comprising maturing the tissue construct in a bioreactor.

6. The method of claim 1, wherein the cells comprise muscle cells, and wherein the method further comprises:
    maturing the tissue construct of pre-aligned microtissues; and
    combining human umbilical vein endothelial cells (hUVECs) with the muscle cells to initiate vascularization of the tissue construct.

7. The method of claim 6, wherein the one or more muscle cells are gut smooth muscle cells (gSMC).

8. The method of claim 1, wherein dispensing the pre-aligned microtissues comprises dispensing, through the nozzle, the bioink such that one pre-aligned microtissue of the pre-aligned microtissues pass through the nozzle at a time in an end-first orientation.

9. The method of claim 8, wherein dispensing the pre-aligned microtissues comprises selecting a flow rate for the bioink through a narrowing passage of the nozzle such that the flow rate of the bioink through the narrowing passage of the nozzle aligns a longitudinal axis of the microtissues with a directional flow of bioink through the narrowing passage of the nozzle.

10. The method of claim 1, wherein dispensing the pre-aligned microtissues comprises depositing the pre-aligned microtissues on a scaffold.

11. The method of claim 8, wherein the nozzle comprises an orifice diameter from about 100 microns to about 200 microns.

12. The method of claim 1, wherein the pre-aligned microtissues have a length to width ratio of at least 3:1.

13. The method of claim 1, wherein dispensing the pre-aligned microtissues comprises printing the pre-aligned microtissues in a volume to create the tissue construct that comprises an anatomical connective tissue.

* * * * *